(12) United States Patent
Jinks et al.

(10) Patent No.: US 8,430,097 B2
(45) Date of Patent: *Apr. 30, 2013

(54) MEDICINAL INHALATION DEVICES AND COMPONENTS THEREOF

(75) Inventors: Philip A. Jinks, Loughborough (GB); Moses M. David, Woodbury, MA (US); Rudolf J. Dams, Antwerp (BE)

(73) Assignee: 3M Innovative Properties Company, St. Paul, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/741,530

(22) PCT Filed: Nov. 6, 2008

(86) PCT No.: PCT/US2008/082593
§ 371 (c)(1),
(2), (4) Date: May 5, 2010

(87) PCT Pub. No.: WO2009/061891
PCT Pub. Date: May 14, 2009

(65) Prior Publication Data
US 2010/0242958 A1    Sep. 30, 2010

Related U.S. Application Data

(60) Provisional application No. 60/985,741, filed on Nov. 6, 2007.

(51) Int. Cl.
*A61M 15/00* (2006.01)
*B05D 3/14* (2006.01)
*B05D 3/00* (2006.01)
*B32B 9/04* (2006.01)

(52) U.S. Cl.
USPC .......... 128/203.12; 128/203.15; 427/2.1; 427/249.7; 427/255.18; 427/387; 427/419.5; 427/578; 428/336; 428/447; 428/450; 428/451

(58) Field of Classification Search ............ 128/203.12, 128/203.15; 427/2.1, 387, 249.7, 255.18, 427/419.5, 578; 428/336, 447, 450, 451
See application file for complete search history.

(56) References Cited

U.S. PATENT DOCUMENTS

| | | | |
|---|---|---|---|
| 3,810,874 | A | 5/1974 | Mitsch |
| 4,991,822 | A | 2/1991 | Enke |
| 5,772,085 | A | 6/1998 | Bryant et al. |
| 6,228,471 | B1 | 5/2001 | Neerinck et al. |
| 6,405,934 | B1 | 6/2002 | Hess et al. |
| 6,596,260 | B1 | 7/2003 | Brugger et al. |
| 6,630,205 | B2 | 10/2003 | Brueck et al. .......... 427/387 |

(Continued)

FOREIGN PATENT DOCUMENTS

| | | |
|---|---|---|
| WO | WO 96/32099 | 10/1996 |
| WO | WO 96/32150 | 10/1996 |

(Continued)

OTHER PUBLICATIONS

International Search Report for PCT/US2008/082593 prepared by the Korean Intellectual Property Office, May 15, 2009.

(Continued)

*Primary Examiner* — D. S. Nakarani

(57) ABSTRACT

A medicinal inhalation device having a non-metal coating coated on at least a portion thereof, and onto which non-metal coating an at least partially fluorinated compound is then covalently bonded.

14 Claims, 5 Drawing Sheets

U.S. PATENT DOCUMENTS

| | | | |
|---|---|---|---|
| 6,649,272 B2 | 11/2003 | Moore et al. .................. 8/447 |
| 6,696,157 B1 | 2/2004 | David et al. | |
| 6,878,419 B2 | 4/2005 | David et al. | |
| 7,094,471 B2 | 8/2006 | Moore et al. .................. 428/447 |
| 7,097,910 B2 | 8/2006 | Moore et al. .................. 8/447 |
| 2003/0031806 A1 | 2/2003 | Jinks | |
| 2003/0089368 A1 | 5/2003 | Zhao | |
| 2003/0103906 A1 | 6/2003 | Ashurst et al. | |
| 2003/0138559 A1 | 7/2003 | Ashurst et al. | |
| 2003/0148030 A1 | 8/2003 | Vernon, Jr. et al. | |
| 2003/0183223 A1 | 10/2003 | Hailey et al. | |
| 2003/0187496 A1 | 10/2003 | Kirk et al. | |
| 2004/0092675 A1 | 5/2004 | Moore et al. .................. 5/533 |
| 2004/0223916 A1 | 11/2004 | Burt et al. | |
| 2005/0061705 A1 | 3/2005 | Spallek et al. | |
| 2005/0133025 A1 | 6/2005 | Laiho et al. | |
| 2012/0103330 A1 | 5/2012 | David et al. .................. 8/203.12 |

FOREIGN PATENT DOCUMENTS

| | | |
|---|---|---|
| WO | WO 96/32151 | 10/1996 |
| WO | WO 96/32345 | 10/1996 |
| WO | WO 99/00315 | 1/1999 |
| WO | WO 99/42154 | 8/1999 |
| WO | WO 01/64273 | 9/2001 |
| WO | WO 01/64274 | 9/2001 |
| WO | WO 01/64275 | 9/2001 |
| WO | WO 01/64524 | 9/2001 |
| WO | WO 02/30498 | 4/2002 |
| WO | WO 02/47829 | 6/2002 |
| WO | WO02/100928 | 12/2002 |
| WO | WO 03/006181 | 1/2003 |
| WO | WO 03/024623 | 3/2003 |
| WO | WO 2004/022142 | 3/2004 |
| WO | WO 2008/051789 | 5/2008 |

OTHER PUBLICATIONS

International Search Report for PCT/US2008/082600 prepared by the Korean Intellectual Property Office, May 22, 2009.

International Search Report for PCT/US2008/082608 prepared by the Korean Intellectual Property Office, May 22, 2009.

International Search Report for PCT/US2008/082614 prepared by the Korean Intellectual Property Office, Jun. 8, 2009.

Partial European Search Report for EP08847413.5 dated Nov. 19, 2010.

MEDICINAL INHALATION DEVICES AND COMPONENTS THEREOF

CROSS REFERENCE TO RELATED APPLICATIONS

This application is a national stage filing under 35 U.S.C. 371 of PCT/US2008/082593, filed Nov. 6, 2008, which claims priority to U.S. Patent Application No. 60/985,741, filed Nov. 6, 2007, the disclosure of which is incorporated by reference in its/their entirety herein.

FIELD OF THE INVENTION

The present invention relates to medicinal inhalation devices and components for such devices as well as methods of making such devices and components.

BACKGROUND OF THE INVENTION

Medicinal inhalation devices, including pressurized inhalers, such as metered dose pressurized inhalers (MDIs), and dry powder inhalers (DPIs), are widely used for delivering medicaments.

Medicinal inhalation devices typically comprise a plurality of hardware components, (which in the case of a MDI can include for example gasket seals; metered dose valves (including their individual components, such as ferrules, valve bodies, valve stems, tanks, springs retaining cups and seals); containers; and actuators) as well as a number of internal surfaces which may be in contact with the medicinal formulation during storage or come in contact with the medicinal formulation during delivery. Often a desirable material for a particular component is found to be unsuitable in regard to its surface properties, e.g. surface energy, and/or its interaction with the medicinal formulation. For example, the relatively high surface energy of materials typically used in MDIs, e.g. acetal polymer for valve stems, or deep drawn stainless steels or aluminum for containers, can cause medicament particles in suspension formulations to adhere irreversibly to the surfaces of corresponding component(s), which has a consequent impact on the uniformity of medicinal delivery. Similar effects are also observed for DPIs. Other examples of potentially undesirable interactions between a component and the medicinal formulation may include enhanced medicament degradation; adsorption of medicament or permeation of a formulation constituent or extraction of chemicals from plastic materials. For DPIs often permeation and adsorption of ambient water pose issues. Also the use of materials having relatively high surface energy for certain components (e.g. metered dose valves and/or individual components thereof), may have undesirable effects for the operation of movable components of a medicinal inhalation device.

Various coatings have been proposed for particular components or surfaces of metered dose inhalers, see e.g. EP 642 992, WO 96/32099, WO 96/32150-1, WO 96/32345, WO 99/42154, WO 02/47829, WO03/024623; WO 02/30498, WO 01/64273; WO 91/64274-5; WO 01/64524; and WO 03/006181.

SUMMARY OF THE INVENTION

Although a number of different coatings have been proposed, there is an ongoing need for medicinal inhalation devices and components thereof having desirable surface properties (e.g. low surface energy) in conjunction with desirable structural integrity (e.g. adhesion, durability, robustness and/or resistance to degradation over the lifetime of the device) of a coating system provided on said devices and components as well as methods of providing such medicinal inhalation devices and components.

In aspects of the present invention there is provided a method of making a medicinal inhalation device or a component of a medicinal inhalation device comprising:
 a) forming a non-metal coating on at least a portion of a surface of the medicinal inhalation device or a component of a medicinal inhalation device, respectively, said coating having at least one functional group;
 b) applying to at least a portion of a surface of the non-metal coating a composition comprising an at least partially fluorinated compound comprising at least one functional group; and
 c) allowing at least one functional group of the at least partially fluorinated compound to react with at least one functional group of the non-metal coating to form a covalent bond.

Additional aspects of the present invention include: devices and components made in accordance with aforesaid methods; a medicinal inhalation device or a component of a medicinal inhalation device comprising a non-metal coating on at least a portion of a surface of the device or the component, respectively, and a fluorine-containing coating bonded to the non-metal coating wherein the fluorine-containing coating comprises an at least partially fluorinated compound comprising at least one functional group which shares at least one covalent bond with the non-metal coating.

The application of such a non-metal coating covalently bonded to an at least partially fluorinated compound as described herein provides desirable surface properties (e.g. low surface energy) in conjunction with desirable structural integrity of the system provided on surfaces of said devices and components.

Such desirable structural integrity can be further enhanced through certain favorable embodiments in which the non-metal coating is substantially free (more favorably free) of fluorine. Alternatively or additionally, structural integrity can be further enhanced in certain favorable embodiments in which the non-metal coating is covalently bonded to the at least a portion of a surface of the device or component. Alternatively or additionally, in other certain favorable embodiments, structural integrity as well as impermeability characteristics can be further facilitated through a non-metal coating that is plasma deposited under ion bombardment conditions.

Further aspects of the present invention include: a medicinal inhalation device or component of a medicinal inhalation device comprising a non-metal coating plasma deposited on at least a portion of a surface of the device or component, respectively, said coating being plasma deposited under ion bombardment conditions and being substantially free (or more favorably) free of fluorine. Other aspects of the present invention include: a medicinal inhalation device or a component of a medicinal inhalation device comprising a diamond-like glass coating on at least a portion of a surface of the device or component, respectively. Such medicinal inhalation devices and components (in particular medicinal inhalation devices comprising such components) show surprisingly desirable surface properties in conjunction with very favorable structural integrity.

Dependent claims define further embodiments of the invention.

The invention, in its various combinations, either in method or apparatus form, may also be characterized by the following listing of items:

1. A method of making a medicinal inhalation device comprising:
   a) forming a non-metal coating on at least a portion of a surface of the device, said coating having at least one functional group;
   b) applying to at least a portion of a surface of the non-metal coating a composition comprising an at least partially fluorinated compound comprising at least one functional group; and
   c) allowing at least one functional group of the at least partially fluorinated compound to react with at least one functional group of the non-metal coating to form a covalent bond.

2. A method of making a component of a medicinal inhalation device comprising:
   a) forming a non-metal coating on at least a portion of a surface of the component, said coating having at least one functional group;
   b) applying to at least a portion of a surface of the non-metal coating a composition comprising an at least partially fluorinated compound comprising at least one functional group; and
   c) allowing at least one functional group of the at least partially fluorinated compound to react with at least one functional group of the non-metal coating to form a covalent bond.

3. A method according to item 1 or item 2, wherein said at least one functional group of the non-metal coating has an active hydrogen.

4. A method according to item 3, wherein said at least one functional group of the non-metal coating having an active hydrogen is selected from the group consisting of a hydroxyl group (—OH), a thiol group (—SH), an amine group (—NH— or —NH$_2$), a carboxyl group (—COOH) or an amide group (—CONH— or —CONH$_2$).

5. A method according to item 4, wherein said at least one functional group of the non-metal coating having an active hydrogen is selected from the group consisting of a hydroxyl group (—OH) and a carboxyl group (—COOH).

6. A method according to item 5, wherein said at least one functional group of the non-metal coating is a hydroxyl group (—OH).

7. A method according to any one of item 1 to 6, wherein said at least one functional group of the non-metal coating is a silanol group (—Si—OH).

8. A method according to any one of items 1 to 7, wherein the non-metal coating comprises a plurality of functional groups.

9. A method according to any one of items 1 to 8, wherein prior to forming the non-metal coating, said surface of the device or the component, as applicable, is exposed to an oxygen or argon plasma, in particular to an oxygen plasma, more particularly an oxygen plasma under ion bombardment conditions.

10. A method according to any one of items 1 to 9, wherein the non-metal coating is formed by plasma deposition.

11. A method according to item 10, wherein the non-metal coating is formed by plasma deposition under ion bombardment conditions.

12. A method according to any one of items 1 to 11, wherein the non-metal coating comprises silicon, oxygen and hydrogen.

13. A method according to item 12, wherein the forming the non-metal coating comprising silicon, oxygen and hydrogen comprises ionizing a gas comprising at least one of an organosilicon or a silicon hydride.

14. A method according to item 13, wherein the gas comprises an organosilicon.

15. A method according to item 14, wherein the organosilicon is selected from the group consisting of trimethylsilane, triethylsilane, trimethoxysilane, triethoxysilane, tetramethylsilane, tetraethylsilane, tetramethoxysilane, tetraethoxysilane, hexamethylcyclotrisiloxane, tetramethylcyclotetrasiloxane, tetraethylcyclotetrasiloxane, octamethylcyclotetrasiloxane, hexamethyldisiloxane, bistrimethylsilylmethane, and mixtures thereof.

16. A method according to item 15, wherein the organosilicon is selected from the group consisting of trimethylsilane, triethylsilane, tetramethylsilane, tetraethylsilane, bistrimethylsilylmethane and mixtures thereof 17. A method according to item 16, wherein the organosilicon is tetramethylsilane.

18. A method according to item 13, wherein the gas comprises a silicon hydride, in particular a silicon hydride selected from the group consisting of SiH$_4$ (silicon tetrahydride), Si$_2$H$_6$ (disilane), and mixtures thereof.

19. A method according to any one of items 13 to 18, wherein the gas further comprises oxygen.

20. A method according to any one of items 12 to 19, wherein the non-metal coating further comprises carbon.

21. A method according to item 20, wherein the non-metal coating is a diamond-like glass containing on a hydrogen free basis at least about 20 atomic percent carbon and at least about 30 atomic percent of silicon+oxygen.

22. A method according to item 21, wherein the diamond-like glass contains on a hydrogen free basis at least about 25 atomic percent carbon, about 15 to about 50 atomic percent of silicon and about 15 to about 50 atomic percent oxygen.

23. A method according to item 22, wherein the diamond-like glass contains on a hydrogen free basis about 30 to about 60 atomic percent carbon, about 20 to about 45 atomic percent of silicon and about 20 to about 45 atomic percent oxygen.

24. A method according to item 23, wherein the diamond-like glass contains on a hydrogen free basis about 30 to about 50 atomic percent carbon, about 25 to about 35 atomic percent of silicon and about 25 to about 45 atomic percent oxygen.

25. A method according to item 24, wherein the diamond-like glass contains on a hydrogen free basis about 30 to about 36 atomic percent carbon, about 26 to about 32 atomic percent of silicon and about 35 to about 41 atomic percent oxygen.

26. A method according to any one of items 12 to 25, wherein the silicon to oxygen ratio in the non-metal coating is less than two.

27. A method according to any one of items 1 to 26, wherein the non-metal coating is exposed to an oxygen plasma or a corona treatment prior to applying the composition comprising an at least partially fluorinated compound comprising at least one functional group, in particular an oxygen plasma, more particular an oxygen plasma under ion bombardment conditions.

28. A method according to any one of items 1 to 27, wherein said at least one functional group of the at least partially fluorinated compound has a hydrolysable group.

29. A method according to any one of items 1 to 28, wherein said at least one functional group of the at least partially fluorinated compound is a silane group.

30. A method according to item 29, wherein the silane group comprises at least one hydrolysable group, in particular at least two hydrolysable groups, and more particularly three hydrolysable groups.

31. A method according to any one of items 1 to 30, wherein said at least partially fluorinated compound comprises a polyfluoropolyether segment, in particular a perfluorinated polyfluoropolyether segment.

32. A method according to any one of item 31, wherein said at least partially fluorinated compound comprises a perfluorinated polyfluoropolyether segment, where in the repeating units of the perfluorinated polyfluoropolyether segment the number of carbon atoms in sequence is at most 6, in particular at most 4, more particular at most 3 and most particular at most 2.

33. A method according to any one of items 1 to 32, wherein the at least partially fluorinated compound comprising at least one functional group is a polyfluoropolyether silane, in particular a multifunctional polyfluoropolyether silane, and more particularly a difunctional polyfluoropolyether silane.

34. A method according to item 33, wherein the polyfluoropolyether segment(s) of the polyfluoropolyether silane is (are) not linked to the functional silane group(s) via a functionality that includes nitrogen-silicon bond or a sulfur-silicon bond.

35. A method according to item 33 or item 34, wherein the polyfluoropolyether segment(s) of the polyfluoropolyether silane is (are) linked to the functional silane group(s) via a functionality that includes a carbon-silicon bond.

36. A method according to item 35, wherein the polyfluoropolyether segment(s) of the polyfluoropolyether silane is (are) linked to the functional silane group(s) via a $—C(R)_2—$Si functionality where R is independently hydrogen or a $C_{1-4}$ alkyl group, more particular hydrogen.

37. A method according to item 36, wherein the polyfluoropolyether segment(s) of the polyfluoropolyether silane is (are) linked to the functional silane group(s) via a $—(CR_2)_k—C(R)_2—$Si functionality where k is at least 2 and where R is independently hydrogen or a $C_{1-4}$ alkyl group, more particular hydrogen.

38. A method according to any one of items 33 to 36, wherein the polyfluoropolyether silane is of Formula Ia:

$$R_f[Q\text{-}[C(R)_2—Si(Y)_{3-x}(R^{1a})_x]_y]_z \qquad \text{Ia}$$

wherein:
  $R_f$ is a monovalent or multivalent polyfluoropolyether segment;
  Q is an organic divalent or trivalent linking group;
  each R is independently hydrogen or a $C_{1-4}$ alkyl group;
  each Y is independently a hydrolysable group;
  $R^{1a}$ is a $C_{1-8}$ alkyl or phenyl group;
  x is 0 or 1 or 2;
  y is 1 or 2; and
  z is 1, 2, 3, or 4.

39. A method according to item 38, wherein the polyfluoropolyether segment, $R_f$, comprises perfluorinated repeating units selected from the group consisting of $—(C_nF_{2n}O)—$, $—(CF(Z)O)—$, $—(CF(Z)C_nF_{2n}O)—$, $—(C_nF_{2n}CF(Z)O)—$, $—(CF_2CF(Z)O)—$, and combinations thereof; wherein n is an integer from 1 to 6 and Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted and wherein for repeating units including Z the number of carbon atoms in sequence is at most 6.

40. A method according to item 39, wherein n is an integer from 1 to 4 and wherein for repeating units including Z the number of carbon atoms in sequence is at most four.

41. A method according to item 39 or item 40, wherein n is an integer from 1 to 3 and wherein for repeating units including Z the number of carbon atoms in sequence is at most three.

42. A method according to any one of items 39 to 41, wherein the polyfluoropolyether segment, $R_f$, comprises perfluorinated repeating units selected from the group consisting of $—(C_nF_{2n}O)—$, $—(CF(Z)O)—$, and combinations thereof; wherein n is 1 or 2 and Z is an $—CF_3$ group.

43. A method according to any one of items 38 to 40, wherein z is 1 and $R_f$ is selected from the group consisting of $C_3F_7O(CF(CF_3)CF_2O)_pCF(CF_3)—$, $CF_3O(C_2F_4O)_pCF_2—$, $C_3F_7O(CF(CF_3)CF_2O)_pCF_2CF_2—$, $C_3F_7O(CF_2CF_2CF_2O)_pCF_2CF_2—$, $C_3F_7O(CF_2CF_2CF_2O)_pCF(CF_3)—$ and $CF_3O(CF_2CF(CF_3)O)_p(CF_2O)X—$, wherein X is $CF_2—$, $C_2F_4—$, $C_3F_6—$, $C_4F_8—$ and wherein the average value of p is 3 to 50.

44. A method according to any one of items 38 to 40, wherein z is 2, and $R_f$ is selected from the group consisting of $—CF_2O(CF_2O)_m(C_2F_4O)_pCF_2—$, $—CF(CF_3)O(CF(CF_3)CF_2O)_pCF(CF_3)—$, $—CF_2O(C_2F_4O)_pCF_2—$, $—(CF_2)_3O(C_4F_8O)_p(CF_2)_3—$, $—CF(CF_3)—(OCF_2CF(CF_3))_pO—C_tF_{2t}—O(CF(CF_3)CF_2O)_pCF(CF_3)—$, wherein t is 2, 3 or 4 and wherein m is 1 to 50, and p is 3 to 40.

45. A method according to item 44, wherein $R_f$ is selected from the group consisting of $—CF_2O(CF_2O)_m(C_2F_4O)_pCF_2—$, $—CF_2O(C_2F_4O)_pCF_2—$, and $—CF(CF_3)—(OCF_2CF(CF_3))_pO—(C_tF_{2t})—O(CF(CF_3)CF_2O)_pCF(CF_3)—$, and wherein t is 2, 3 or 4, and wherein the average value of m+p or p+p or p is from about 4 to about 24.

46. A method according to any one of items 38 to 45, wherein Q is selected from the group consisting of $—C(O)N(R)—(CH_2)_k—$, $—S(O)_2N(R)—(CH_2)_k—$, $—(CH_2)_k—$, $—CH_2O—(CH_2)_k—$, $—C(O)S—(CH_2)_k—$, $—CH_2OC(O)N(R)—(CH_2)_k—$, and

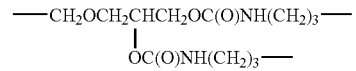

wherein R is hydrogen or $C_{1-4}$ alkyl, and k is 2 to about 25.

47. A method according to item 46, wherein Q is selected from the group consisting of $—C(O)N(R)(CH_2)_2—$, $—OC(O)N(R)(CH_2)_2—$, $—CH_2O(CH_2)_2—$, or $—CH_2—OC(O)N(R)—(CH_2)_2—$, wherein R is hydrogen or $C_{1-4}$ alkyl and y is 1.

48. A method according to any one of items 36 to 47, wherein R is hydrogen.

49. A method according to any one of items 38 to 48, wherein x is 0.

50. A method according to item 28 or item 30 or any one of items 38 to 49, wherein each hydrolysable group is independently selected from the group consisting of hydrogen, halogen, alkoxy, acyloxy, polyalkyleneoxy, and aryloxy groups.

51. A method according to item 50, wherein each hydrolysable group is independently selected from the group consisting of alkoxy, acyloxy, aryloxy, and polyalkyleneoxy groups.

52. A method according to item 50 or item 51, wherein each hydrolysable group is independently an alkoxy group, in particular an alkoxy group $—OR'$ wherein each R' is independently a $C_{1-6}$ alkyl, more particularly a $C_{1-4}$ alkyl.

53. A method according to any one of items 38 to 42 or any one of items of items 44 to 52, wherein $R_f$ is $—CF_2O(CF_2O)_m(C_2F_4O)_pCF_2—$, and Q-C(R)_2—Si(Y')_{3-x}(R^{1a})_x$ is $C(O)NH(CH_2)_3Si(OR')_3$, wherein R' is methyl or ethyl and wherein m is 1 to 50 and p is 3 to 40, in particular wherein the average value of m+p or p+p or p is from about 4 to about 24, more particularly wherein m and p are each about 9 to 12.

54. A method according to any one of items 31 to 53, wherein the weight average molecular weight of the polyfluoropolyether segment is about 1000 or higher, in particular about 1800 or higher.

55. A method according to any one of items 33 to 53, wherein the amount of polyfluoropolyether silane having a polyfluoropolyether segment having a weight average molecular weight less than 750 is not more than 10% by weight of total amount of polyfluoropolyether silane, in particular not more than 5% by weight of total amount of polyfluoropolyether silane, more particularly not more than 1% by weight of total amount of polyfluoropolyether silane, and most particular 0% by weight of total amount of polyfluoropolyether silane.

56. A method according to any one of items 30 to 55 as dependent directly or indirectly on item 5 or item 6, wherein the non-metal coating is substantially free of amine, amido and/or thiol functional groups, in particular the non-metal coating is free of amine, amido and/or thiol functional groups 57. A method according to any one of items 1 to 56, wherein the non-metal coating is substantially free of fluorine, in particular free of fluorine.

58. A method according to any one of items 1 to 57, wherein the composition comprising an at least partially fluorinated compound comprising at least one a functional group further comprises an organic solvent.

59. A method according to item 58, wherein the organic solvent is a fluorinated solvent and/or a lower alcohol.

60. A method according to item 58 or item 59, wherein the composition comprising an at least partially fluorinated compound comprising at least one a functional group further comprises an acid.

61. A method according to any one of items 1 to 60, wherein the composition comprising an at least partially fluorinated compound comprising at least one functional group further comprises water.

62. A method according to any one of items 1 to 61, wherein the composition comprising an at least partially fluorinated compound comprising at least one functional group further comprises a non-fluorinated cross-linking agent, in particular a cross-linking agent comprising one or more non-fluorinated compounds, each compound having at least two hydrolysable groups per molecule.

63. A method according to item 62, wherein the non-fluorinated compound is a compound in accordance to Formula II:

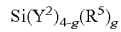   II where $R^5$ represents a non-hydrolysable group;
$Y^2$ represents a hydrolysable group; and
g is 0, 1 or 2.

64. A method according to item 62 or 63, wherein the cross-linking agent comprises a compound selected from group consisting of tetramethoxysilane, tetraethoxysilane, tetrapropoxysilane, tetrabutoxysilane, methyl triethoxysilane, dimethyldiethoxysilane, octadecyltriethoxy-silane, 3-glycidoxypropyltriethoxysilane, 3-aminopropyl-trimethoxysilane, 3-aminopropyltriethoxysilane 3-trimethoxysilylpropylmethacrylate, and mixtures thereof.

65. A method according to any one of items 1 to 64, wherein the composition comprising an at least partially fluorinated compound comprising at least one functional group is applied by spraying, dipping, rolling, brushing, spreading, spin coating or flow coating, in particular by spraying or dipping.

66. A method according to any one of items 1 to 65, wherein after applying the composition, the method further comprises a step of curing.

67. A method according to item 66, wherein the curing is carried out at an elevated temperature in the range from about 40° C. to about 300° C.

68. A method according to any one of items 1 to 67, wherein the non-metal coating is formed on said surface of the device or said surface of the component of the device, as applicable, such that the non-metal coating is covalently bonded to said surface.

69. A method according to any one of items 1 to 68, where said surface of the device or said surface of the component of the device, as applicable, is a surface that is or will come in contact with a medicament or a medicinal formulation during storage or delivery from the medicinal inhalation device.

70. A method according to any one of items 1 to 69, where said surface of the device or said surface of the component of the device, as applicable, is a surface that comes in contact with a movable component of the device or is a surface of a movable component of the device.

71. A method according to any one of items 1 to 70, where said medicinal inhalation device is a metered dose inhaler or a dry powder inhaler.

72. A medicinal inhalation device made according to item 1 or any one of items 3 to 71 as directly or indirectly dependent on item 1.

73. A component of a medical inhalation device made according to item 2 or any one of items 3 to 71 as directly or indirectly dependent on item 2.

74. A medicinal inhalation device comprising a non-metal coating on at least a portion of a surface of the device and a fluorine-containing coating bonded to the non-metal coating wherein the fluorine-containing coating comprises an at least partially fluorinated compound comprising at least one functional group which shares at least one covalent bond with the non-metal coating.

75. A component of a medicinal inhalation device comprising a non-metal coating on at least a portion of a surface of the component, and a fluorine-containing coating bonded to the non-metal coating wherein the fluorine-containing coating comprises an at least partially fluorinated compound comprising at least one functional group which shares at least one covalent bond with the non-metal coating.

76. A device according to item 74 or a component according to item 75, wherein the fluorine-containing coating is covalently bonded to the non-metal coating through a plurality of covalent bonds.

77. A device according to item 74 or item 76 as dependent on item 74 or a component according to item 75 or item 76 as dependent on item 75, wherein the fluorine-containing coating is covalently bonded to the non-metal coating through a plurality of covalent bonds including bonds in O—Si groups, in particular bonds in Si—O—Si groups.

78. A device according to item 74 or any of one of items 76 to 77 as directly or indirectly dependent on item 74, or a component according to item 75 or any of one items 76 to 77 as directly or indirectly dependent on item 75, wherein the non-metal coating comprises silicon and oxygen.

79. A device according to item 78 as directly or indirectly dependent on item 74, or a component according to item 78 as directly or indirectly dependent on item 75, wherein the non-metal coating further comprises carbon.

80. A device according to item 78 or 79 as directly or indirectly dependent on item 74, or a component according to item 78 or 79 as directly or indirectly dependent on item 75, wherein the silicon to oxygen ratio in the non-metal coating is less than two.

81. A device according to item 74 or any of one of items 76 to 80 as directly or indirectly dependent on item 74, or a component according to item 75 or any of one of items 76 to 80 as directly or indirectly dependent on item 75, wherein the non-metal coating is substantially free of fluorine, more particularly free of fluorine.

82. A device according to item 74 or any one of items 76 to 81 as directly or indirectly dependent on item 74, or a component according to item 75 or any one of items 76 to 81 as directly or indirectly dependent on item 75, wherein the non-metal coating is covalently bonded to the at least a portion of a surface of the device or the component, respectively.

83. A device according to item 74 or any one of items 76 to 82 as directly or indirectly dependent on item 74, or a component according to item 75 or any of one of items 76 to 82 as directly or indirectly dependent on item 75, wherein the non-metal coating is a plasma-deposited coating.

84. A device according to item 83 as directly or indirectly dependent on item 74, or a component according to item 83 as directly or indirectly dependent on item 75, wherein the non-metal coating is a plasma-deposited coating deposited under conditions of ion bombardment.

85. A device according to item 74 or any one of items 76 to 84 as directly or indirectly dependent on item 74, or a component according to item 75 or any one of items 76 to 84 as directly or indirectly dependent on item 75, wherein the non-metal coating is a diamond-like glass coating.

86. A device according to item 85 as directly or indirectly dependent on item 74, or a component according to item 85 as directly or indirectly dependent on item 75, wherein the diamond-like glass coating contains on a hydrogen free basis at least about 20 atomic percent carbon and at least about 30 atomic percent of silicon+oxygen.

87. A device according to item 86 as directly or indirectly dependent on item 74, or a component according to item 86 as directly or indirectly dependent on item 75, wherein the diamond-like glass coating contains on a hydrogen free basis at least about 25 atomic percent carbon, about 15 to about 50 atomic percent of silicon and about 15 to about 50 atomic percent oxygen.

88. A device according to item 87 as directly or indirectly dependent on item 74, or a component according to item 87 as directly or indirectly dependent on item 75, wherein the diamond-like glass coating contains on a hydrogen free basis about 30 to about 60 atomic percent carbon, about 20 to about 45 atomic percent of silicon and about 20 to about 45 atomic percent oxygen.

89. A device according to item 88 as directly or indirectly dependent on item 74, or a component according to item 88 as directly or indirectly dependent on item 75, wherein the diamond-like glass coating contains on a hydrogen free basis about 30 to about 50 atomic percent carbon, about 25 to about 35 atomic percent of silicon and about 25 to about 45 atomic percent oxygen.

90 A device according to item 89 as directly or indirectly dependent on item 74, or a component according to item 89 as directly or indirectly dependent on item 75, wherein the diamond-like glass coating contains on a hydrogen free basis about 30 to about 36 atomic percent carbon, about 26 to about 32 atomic percent of silicon and about 35 to about 41 atomic percent oxygen.

91. A device according to item 74 or any of one of items 76 to 90 as directly or indirectly dependent on item 74, or a component according to item 75 or any of one of items 76 to 90 as directly or indirectly dependent on item 75, wherein the at least one functional group of the at least partially fluorinated compound is a silane group.

92. A device according to item 74 or any of one of items 76 to 91 as directly or indirectly dependent on item 74, or a component according to item 75 or any of one of items 76 to 91 as directly or indirectly dependent on item 75, wherein the at least partially fluorinated compound comprises a polyfluoropolyether segment, in particular a perfluorinated polyfluoropolyether segment.

93. A device according to item 74 or any of one of items 76 to 92 as directly or indirectly dependent on item 74, or a component according to item 75 or any of one of items 76 to 92 as directly or indirectly dependent on item 75, wherein the at least partially fluorinated compound comprises a perfluorinated polyfluoropolyether segment, where in the repeating units of the perfluorinated polyfluoropolyether segment the number of carbon atoms in sequence is at most 6, in particular at most 4, more particular at most 3 and most particular at most 2.

94. A device according to item 74 or any of one of items 76 to 93 as directly or indirectly dependent on item 74, or a component according to item 75 or any of one of items 76 to 93 as directly or indirectly dependent on item 75, wherein the at least partially fluorinated compound comprising at least one functional group is a polyfluoropolyether silane, in particular a multifunctional polyfluoropolyether silane, and more particularly a difunctional polyfluoropolyether silane.

95. A device according to item 94 as directly or indirectly dependent on item 74, or a component according to item 94 as directly or indirectly dependent on item 75, wherein the polyfluoropolyether segment(s) is (are) not linked to the silane group(s) via a functionality that includes nitrogen-silicon bond or a sulfur-silicon bond.

96. A device according to item 94 or item 95 as directly or indirectly dependent on item 74, or a component according to item 94 or item 95 as directly or indirectly dependent on item 75, wherein the polyfluoropolyether segment(s) is (are) linked to the silane group(s) via a functionality that includes a carbon-silicon bond, in particular via a —$C(R)_2$—Si functionality where R is independently hydrogen or a $C_{1-4}$ alkyl group, more particular via a —$(CR_2)_k$—$C(R)_2$—Si functionality where k is at least 2 and where R is independently hydrogen or a $C_{1-4}$ alkyl group.

97. A device according to item 94 or item 95 as directly or indirectly dependent on item 74, or a component according to item 94 or item 95 as directly or indirectly dependent on item 75, wherein the fluorine-containing coating is a polyfluoropolyether-containing coating comprising polyfluoropolyether silane entities of the following Formula Ib:

$$R_f[Q-[C(R)_2—Si(O—)_{3-x}(R^{1a})_x]_y]_z \qquad \text{Ib}$$

which shares at least one covalent bond with the non-metal coating; and
wherein:
R$_f$ is a monovalent or multivalent polyfluoropolyether segment;
Q is an organic divalent or trivalent linking group;
each R is independently hydrogen or a $C_{1-4}$ alkyl group;
$R^{1a}$ is a $C_{1-8}$ alkyl or phenyl group;
x is 0 or 1 or 2;
y is 1 or 2; and
z is 1, 2, 3, or 4.

98. A device according to item 97 as directly or indirectly dependent on item 74, or a component according to item 97 as directly or indirectly dependent on item 75, wherein the at least on covalent bond shared with the non-metal coating is a bond to an oxygen atom in Si(O—)$_{3-x}$.

99. A device according to item 97 or item 98 as directly or indirectly dependent on item 74, or a component according to item 97 or item 98 as directly or indirectly dependent on item 75, wherein the polyfluoropolyether segment, R$_f$, comprises perfluorinated repeating units selected from the group consisting of —$(C_nF_{2n}O)$—, —(CF(Z)O)—, —(CF(Z)C$_n$F$_{2n}$O)—, —(C$_n$F$_{2n}$CF(Z)O)—, —(CF$_2$CF(Z)O)—, and combinations thereof; wherein n is an integer from 1 to 6 and Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted and wherein for repeating units including Z the number of carbon atoms in sequence is at most 6.

100. A device according to item 99 as directly or indirectly dependent on item 74, or a component according to item 99 as directly or indirectly dependent on item 75, wherein n is an integer from 1 to 4 and wherein for repeating units including Z the number of carbon atoms in sequence is at most four.

101. A device according to item 100 as directly or indirectly dependent on item 74, or a component according to item 100 as directly or indirectly dependent on item 75, wherein n is an integer from 1 to 3 and wherein for repeating units including Z the number of carbon atoms in sequence is at most three, more particularly the polyfluoropolyether segment, R$_f$, comprises perfluorinated repeating units selected from the group consisting of —(C$_n$F$_{2n}$O)—, —(CF(Z)O)—, and combinations thereof; wherein n is 1 or 2 and Z is an —CF$_3$ group.

102. A device according to any one of items 97 to 100 as directly or indirectly dependent on item 74, or a component according to any one of items 97 to 100 as directly or indirectly dependent on item 75, wherein z is 1 and R$_f$ is selected from the group consisting of C$_3$F$_7$O(CF(CF$_3$)CF$_2$O)$_p$CF(CF$_3$)—, CF$_3$O(C$_2$F$_4$O)$_p$CF$_2$—, C$_3$F$_7$O(CF(CF$_3$)CF$_2$O)$_p$CF$_2$CF$_2$—, C$_3$F$_7$O(CF$_2$CF$_2$CF$_2$O)$_p$CF$_2$CF$_2$—, C$_3$F$_7$O(CF$_2$CF$_2$CF$_2$O)$_p$CF(CF$_3$)— and CF$_3$O(CF$_2$CF(CF$_3$)O)$_p$(CF$_2$O)X—, wherein X is CF$_2$—, C$_2$F$_4$—, C$_3$F$_6$—, C$_4$F$_8$— and wherein the average value of p is 3 to 50.

103. A device according to any one of items 97 to 100 as directly or indirectly dependent on item 74, or a component according to any one of items 97 to 101 as directly or indirectly dependent on item 75, wherein z is 2, and R$_f$ is selected from the group consisting of —CF$_2$O(CF$_2$O)$_m$(C$_2$F$_4$O)$_p$CF$_2$—, —CF(CF$_3$)O(CF(CF$_3$)CF$_2$O)$_p$CF(CF$_3$)— —CF(CF$_3$)—(OCF$_2$CF(CF$_3$))$_p$O—C$_t$F$_{2t}$—O(CF(CF$_3$)CF$_2$O)$_p$CF(CF$_3$)—, —CF$_2$O(C$_2$F$_4$O)$_p$CF$_2$—, —(CF$_2$)$_3$O(C$_4$F$_8$O)$_p$(CF$_2$)$_3$—, wherein t is 2, 3 or 4 and wherein m is 1 to 50, and p is 3 to 40.

104. A device according to item 103 as directly or indirectly dependent on item 74, or a component according to item 103 as directly or indirectly dependent on item 75, wherein R$_f$ is selected from the group consisting of —CF$_2$O(CF$_2$O)$_m$(C$_2$F$_4$O)$_p$CF$_2$—, —CF$_2$O(C$_2$F$_4$O)$_p$CF$_2$—, and —CF(CF$_3$)—(OCF$_2$CF(CF$_3$))$_p$O—(C$_t$F$_{2t}$)—O(CF(CF$_3$)CF$_2$O)$_p$CF(CF$_3$)—, and wherein t is 2, 3 or 4, and wherein the average value of m+p or p+p or p is from about 4 to about 24.

105. A device according to any one of items 97 to 104 as directly or indirectly dependent on item 74, or a component according to any one of items 97 to 104 as directly or indirectly dependent on item 75, wherein Q is selected from the group consisting of —C(O)N(R)—(CH$_2$)$_k$—, —S(O)$_2$N(R)—(CH$_2$)$_k$—, —(CH$_2$)$_k$—, —CH$_2$O—(CH$_2$)$_k$—, —C(O)S—(CH$_2$)$_k$—, —CH$_2$OC(O)N(R)—(CH$_2$)$_k$—, and

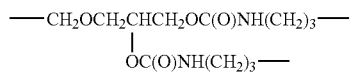

wherein R is hydrogen or C$_{1-4}$ alkyl, and k is 2 to about 25.

106. A device according to item 105 as directly or indirectly dependent on item 74, or a component according to item 105 as directly or indirectly dependent on item 75, wherein Q is selected from the group consisting of —C(O)N(R)(CH$_2$)$_2$—, —OC(O)N(R)(CH$_2$)$_2$—, —CH$_2$O(CH$_2$)$_2$—, or —CH$_2$—OC(O)N(R)—(CH$_2$)$_2$—, wherein R is hydrogen or C$_{1-4}$ alkyl and y is 1.

107. A device according to any one of items 96 to 106 as directly or indirectly dependent on item 74, or a component according to any one of items 96 to 106 as directly or indirectly dependent on item 75, wherein R is hydrogen.

108. A device according to any one of items 97 to 107 as directly or indirectly dependent on item 74, or a component according to any one of items 97 to 107 as directly or indirectly dependent on item 75, wherein x is 0.

109. A device according to any one of items 97 to 101 or any one of items 103 to 108 as directly or indirectly dependent on item 74, or a component according to any one of items 97 to 101 or any one of items 103 to 108 as directly or indirectly dependent on item 75, wherein R$_f$ is —CF$_2$O(CF$_2$O)$_m$(C$_2$F$_4$O)$_p$CF$_2$—, and Q-C(R)$_2$—Si(O—)$_{3-x}$(R$^{1a}$)$_x$ is C(O)NH(CH$_2$)$_3$Si(O—)$_3$ and wherein m is 1 to 50 and p is 3 to 40, in particular wherein the average value of m+p or p+p or p is from about 4 to about 24, more particularly wherein m and p are each about 9 to 12.

110. A device according to any one of items 92 to 109 as directly or indirectly dependent on item 74, or a component according to any one of items 92 to 109 as directly or indirectly dependent on item 75, wherein the weight average molecular weight of the polyfluoropolyether segment is about 1000 or higher, in particular about 1800 or higher.

111. A device according to any one of items 92 to 110 as directly or indirectly dependent on item 74, or a component according to any one of items 92 to 110 as directly or indirectly dependent on item 75, wherein the weight average molecular weight of the polyfluoropolyether segment is about 6000 or less, in particular about 4000 or less.

112. A device according to any one of items 94 to 111 as directly or indirectly dependent on item 74, or a component according to any one of items 94 to 111 as directly or indirectly dependent on item 75, wherein the amount of polyfluoropolyether silane having a polyfluoropolyether segment having a weight average molecular weight less than 750 is not more than 10% by weight of total amount of polyfluoropolyether silane, in particular not more than 5% by weight of total amount of polyfluoropolyether silane, more particularly not more than 1% by weight of total amount of polyfluoropolyether silane, and most particular 0% by weight of total amount of polyfluoropolyether silane.

113. A device according to any one of items 91 to 112 as directly or indirectly dependent on item 74, or a component according to any one of items 92 to 112 as directly or indirectly dependent on item 75, wherein the non-metal coating is substantially free of nitrogen and/or sulfur, in particular free of nitrogen and/or sulfur.

114. A medicinal inhalation device comprising a non-metal coating plasma deposited on at least a portion of a surface of the device, said coating being plasma deposited under ion bombardment conditions and being substantially free of fluorine, in particular free of fluorine.

115. A component of a medicinal inhalation device comprising a non-metal coating plasma deposited on at least a portion of a surface of the component, said coating being plasma deposited under ion bombardment conditions and being substantially free of fluorine, in particular free of fluorine.

116. A device according to item 114 or a component according to item 115, wherein the non-metal coating is covalently bonded to the at least a portion of a surface of the device or the component, respectively.

117. A device according to item 114 or item 116 as dependent on item 114, or a component according to item 115 or item 116 as dependent on item 115, wherein the non-metal coating comprises silicon, oxygen and hydrogen.

118. A device according to item 117 as directly or indirectly dependent on item 114, or a component according to item 117 as directly or indirectly dependent on item 115, wherein the non-metal coating further comprises carbon.

119. A device according to item 117 or item 118 as directly or indirectly dependent on item 114, or a component according to item 117 or item 118 as directly or indirectly dependent on item 115, wherein the silicon to oxygen ratio in the non-metal coating is less than two.

120. A medicinal inhalation device comprising a diamond-like glass coating on at least a portion of a surface of the device.

121. A component of a medicinal inhalation device comprising a diamond-like glass coating on at least a portion of a surface of the component.

122. A device according to item 120, or a component according to item 121, wherein the diamond-like glass coating contains on a hydrogen free basis at least about 20 atomic percent carbon and at least about 30 atomic percent of silicon+oxygen.

123. A device according to item 122 as dependent on item 120, or a component according to item 122 as dependent on item 121, wherein the diamond-like glass coating contains on a hydrogen free basis at least about 25 atomic percent carbon, about 15 to about 50 atomic percent of silicon and about 15 to about 50 atomic percent oxygen.

124. A device according to item 123 as directly or indirectly dependent on item 120, or a component according to item 123 as directly or indirectly dependent on item 121, wherein the diamond-like glass coating contains on a hydrogen free basis about 30 to about 60 atomic percent carbon, about 20 to about 45 atomic percent of silicon and about 20 to about 45 atomic percent oxygen.

125. A device according to item 124 as directly or indirectly dependent on item 120, or a component according to item 124 as directly or indirectly dependent on item 121, wherein the diamond-like glass coating contains on a hydrogen free basis about 30 to about 50 atomic percent carbon, about 25 to about 35 atomic percent of silicon and about 25 to about 45 atomic percent oxygen.

126. A device according to item 125 as directly or indirectly dependent on item 120, or a component according to item 125 as directly or indirectly dependent on item 121, wherein the diamond-like glass coating contains on a hydrogen free basis about 30 to about 36 atomic percent carbon, about 26 to about 32 atomic percent of silicon and about 35 to about 41 atomic percent oxygen.

127. A device according to item 120 or any one of items 122 to 126 as directly or indirectly dependent on item 120, or a component according to item 120 or any one of items 122 to 126 as directly or indirectly dependent on item 121, wherein the silicon to oxygen ratio in the diamond-like glass coating is less than two.

128. A device or a component according to any one of items 74 to 127, as applicable, where said surface of the device or said surface of the component of the device, as applicable, is a surface that is or will come in contact with a medicament or a medicinal formulation during storage or delivery from the medicinal inhalation device.

129. A device or a component according to any one of items 74 to 128, as applicable, where said surface of the device or said surface of the component of the device, as applicable, is a surface that comes in contact with a movable component of the device or is a surface of a movable component of the device.

130. A device or a component according to any one of items 74 to 129 where said medicinal inhalation device is a metered dose inhaler or a dry powder inhaler.

131. A component according to item 73 or item 75 or any one of items 76 to 113 as directly or indirectly dependent on item 75 or item 115 or any one of items 116 to 119 as directly or indirectly dependent on item 115 or item 121 or any one of items 122 to 127 as directly or indirectly dependent on item 121, wherein the component is a component of a metered dose inhaler and the component is selected from the group consisting of an actuator, an aerosol container, a ferrule, a valve body, a valve stem and a compression spring.

132. A component according to item 73 or item 75 or any one of items 76 to 113 as directly or indirectly dependent on item 75 or item 115 or any one of items 116 to 119 as directly or indirectly dependent on item 115 or item 121 or any one of items 122 to 127 as directly or indirectly dependent on item 121, wherein the component is a component of a dry powder inhaler and the component is selected from the group consisting of a powder container, an component used to open sealed powder container, a component that defines at least in part a deagglomeration chamber, a component of a deaglomeration system, a component that defines at least in part a flow channel, a dose-transporting component, a component that defines at least in part a mixing chamber, a component that defines at least in part an actuation chamber, a mouthpiece and a nosepiece.

133. A component according to item 73 or item 75 or any one of items 76 to 113 as directly or indirectly dependent on item 75 or item 115 or any one of items 116 to 119 as directly or indirectly dependent on item 115 or item 121 or any one of items 122 to 127 as directly or indirectly dependent on item 121, wherein the component is a component of a breath-actuating device or a component of a breath-coordinating device or a spacer or a component of a spacer or a component of a dose counter for a medicinal inhalation device.

134. A device according to item 72 or item 74 or any one of items 76 to 113 as directly or indirectly dependent on item 74 or item 114 or any one of items 116 to 119 as directly or indirectly dependent on item 114 or item 120 or any one of items 122 to 127 as directly or indirectly dependent on item 120, wherein the device is a metered dose inhaler and the inhaler contains a medicinal aerosol formulation comprising a medicament and HFA 134a and/or HFA 227

135. A device according to item 134, wherein the medicinal aerosol formulation is substantially free of ethanol.

136. A device according to item 135, wherein the medicinal aerosol formulation is free of ethanol.

137. A device according to any one of items 134 to 136, wherein the medicinal aerosol formulation is substantially free of surfactant.

138. A device according to item 137, wherein the medicinal aerosol formulation is free of surfactant.

139. A device according to any one of items 134 to 138, wherein the medicinal aerosol formulation comprises a medicament that is dispersed said formulation.

140. A device according to any one of items 134 to 139, wherein the medicinal aerosol formulation medicinal formulation comprises a medicament selected from the group consisting of albuterol, terbutaline, ipratropium, oxitropium, tiotropium, beclomethasone, flunisolide, budesonide, mometasone, ciclesonide, cromolyn sodium, nedocromil sodium, ketotifen, azelastine, ergotamine, cyclosporine, salmeterol, fluticasone, formoterol, procaterol, indacaterol, TA2005, omalizumab, zileuton, insulin, pentamidine, calcitonin, leuprolide, alpha-1-antitrypsin, interferon, triamcinolone, and pharmaceutically acceptable salts and esters thereof and mixtures thereof.

The above summary of the present invention is not intended to describe each disclosed embodiment or every implementation of the present invention. The description that follows more particularly exemplifies illustrative embodiments. In several places throughout the application, guidance is provided through lists of examples, which examples can be used individually and in various combinations. In each instance, the recited list serves only as a representative group and should not be interpreted as an exclusive list

BRIEF DESCRIPTION OF DRAWINGS

The invention will now be described with reference to the accompanying drawings in which.

DETAILED DESCRIPTION

It is to be understood that the present invention covers all combinations of particular, suitable, desirable, favorable, advantageous and preferred aspects of the invention described herein.

Figure 1A:
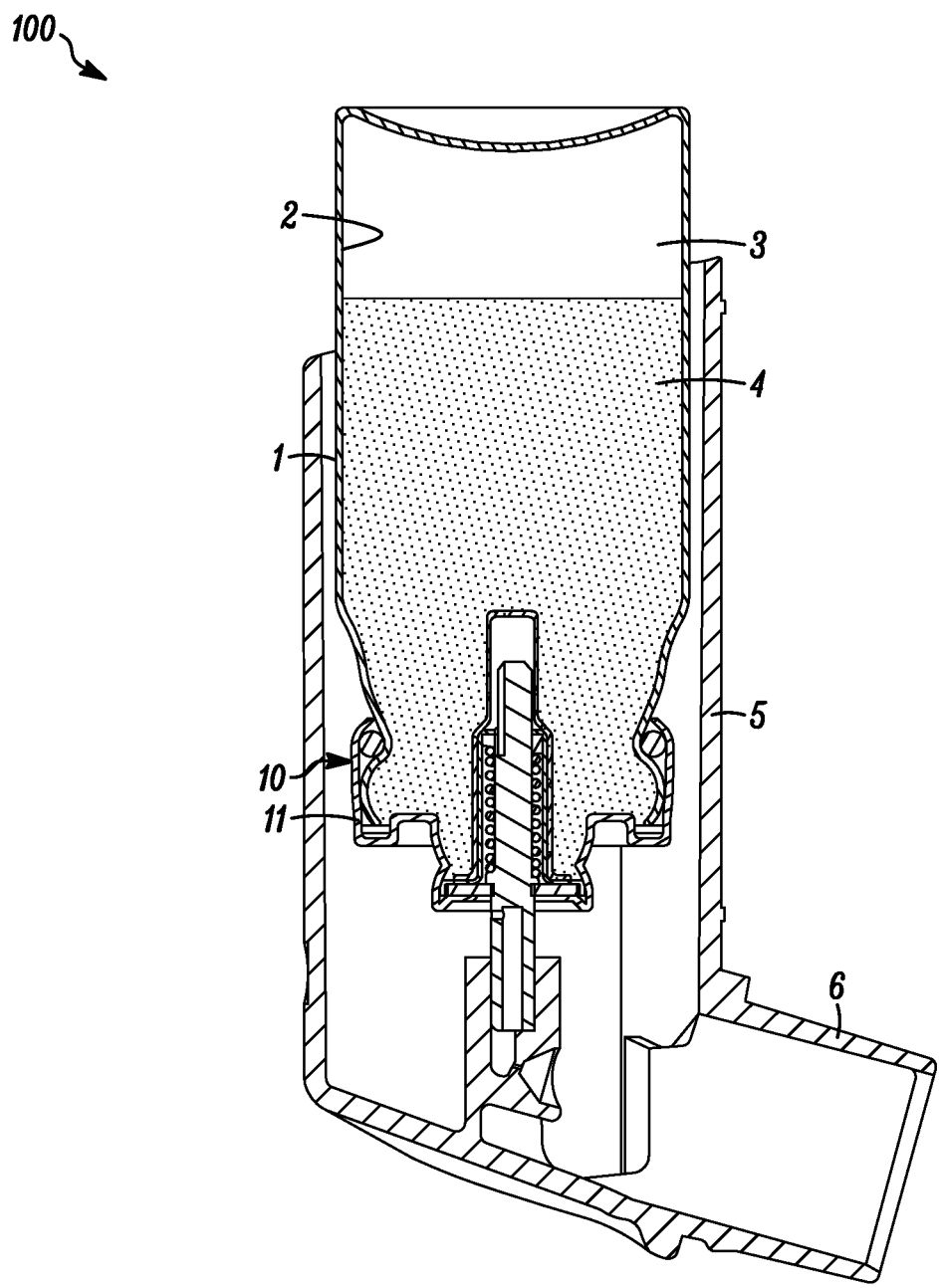
FIG. 1a represents a schematic cross-sectional view of a pressurized metered dose inhaler known in the art and FIG. 1b represents an enlarged view of a portion of the inhaler.

For better understanding of the present invention, in the following an exemplary, well known pressurized metered dose inhaler (FIG. 1) as well as several known metered dose valves for pressurized metered dose inhalers (FIGS. 2 to 5) will be first described. In particular, FIG. 1a shows a metered dose dispenser (100), in particular an inhaler, including an aerosol container (1) fitted with a metered dose valve (10) (shown in its resting position).

Aerosol containers for metered dose inhalers are typically made of aluminum or an aluminum alloy. Aerosol containers may be made of other materials, such as stainless steel, glass, plastic and ceramics.

Returning to FIG. 1a, the valve is typically affixed onto the container via a cap or ferrule (11) (typically made of aluminum or an aluminum alloy) which is generally provided as part of the valve assembly. The illustrated valve is a commercial valve marketed under the trade designation SPRAYMISER by 3M Company, St. Paul, Minn., USA. As shown in FIG. 1a, the container/valve dispenser is typically provided with an actuator (5) including an appropriate patient port (6), such as a mouthpiece. For administration to the nasal cavities the patient port is generally provided in an appropriate form (e.g. smaller diameter tube, often sloping upwardly) for delivery through the nose. Actuators are generally made of a plastic, for example polypropylene or polyethylene. As can be seen from FIG. 1a, the inner walls (2) of the container and the outer walls of the portion(s) of the metered dose valve located within the container defined a formulation chamber (3) in which aerosol formulation (4) is contained. Depending on the particular metered dose valve and/or filling system, aerosol formulation may be filled into the container either by cold-filling (in which chilled formulation is filled into the container and subsequently the metered dose valve is fitted onto the container) or by pressure filling (in which the metered dose valve is fitted onto the container and then formulation is pressure filled through the valve into the container).

An aerosol formulation used in a metered dose inhaler typically comprises a medicament or a combination of medicaments and liquefied propellant selected from the group consisting of HFA 134a, HFA 227 and mixtures thereof. Aerosol formulations may, as desired or needed, comprise other excipients, such as surfactant, a co-solvent (e.g. ethanol), $CO_2$, or a particulate bulking agent. Medicament may be provided in particulate form (generally having a median size in the range of 1 to 10 microns) suspended in the liquefied propellant. Alternatively medicament may be in solution (e.g. dissolved) in the formulation. In the event a combination of two or more medicaments is included, all the medicaments may be suspended or in solution or alternatively one or more medicaments may be suspended, while one or more medicaments may be in solution. A medicament may be a drug, vaccine, DNA fragment, hormone or other treatment. The amount of medicament would be determined by the required dose per puff and available valve sizes, which are typically 25, 50 or 63 microliters, but may include 100 microliters where particularly large doses are required. Suitable drugs include those for the treatment of respiratory disorders, e.g., bronchodilators, anti-inflammatories (e.g. corticosteroids), anti-allergies, anti-asthmatics, anti-histamines, and anti-cholinergic agents. Therapeutic proteins and peptides may also be employed for delivery by inhalation. Exemplary drugs which may be employed for delivery by inhalation include but are not limited to: albuterol, terbutaline, ipratropium, oxitropium, tiotropium, beclomethasone, flunisolide, budesonide, mometasone, ciclesonide, cromolyn sodium, nedocromil sodium, ketotifen, azelastine, ergotamine, cyclosporine, salmeterol, fluticasone, formoterol, procaterol, indacaterol, TA2005, omalizumab, zileuton, insulin, pentamidine, calcitonin, leuprolide, alpha-1-antitrypsin, interferons, triamcinolone, and pharmaceutically acceptable salts and esters thereof such as albuterol sulfate, formoterol fumarate, salmeterol xinafoate, beclomethasone dipropionate, triamcinolone acetonide, fluticasone propionate, tiotropium bromide, leuprolide acetate and mometasone furoate.

Embodiments, described in detail below, in accordance with the present invention are particularly useful in regard to metered dose inhalers including a medicinal aerosol formulation that include low amounts of surfactant (0.005 wt % with respect to the formulation); or is substantially free (less than 0.0001 wt % with respect to drug) or free of a surfactant. Alternatively or additionally, embodiments described in detail below, are particularly useful in metered dose inhalers including a medicinal aerosol formulation that contains low amounts of ethanol (less than 5 wt % with respect to the formulation), or is substantially free (less than 0.1 wt % with respect to the formulation) or free of ethanol.

Figure 1B:
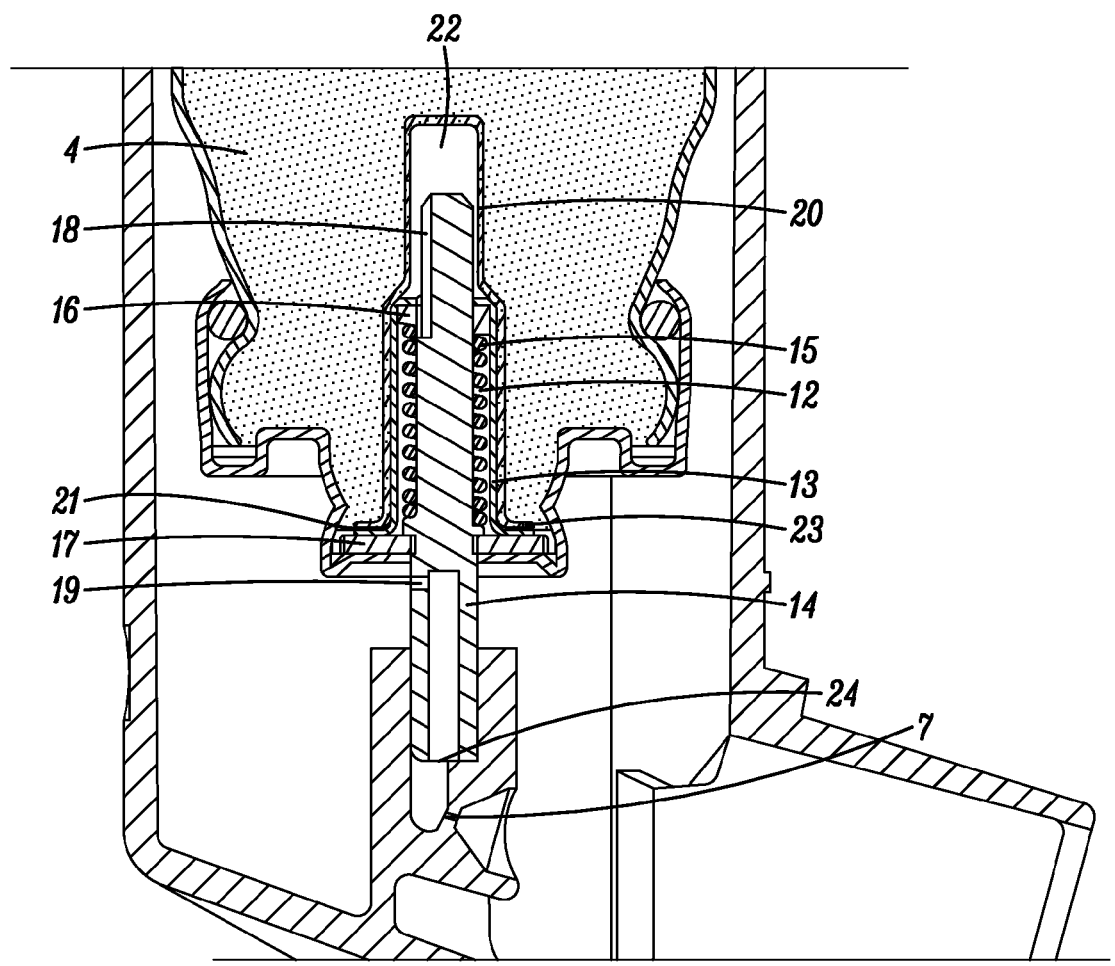

The valve shown in FIG. 1a, better viewed in FIG. 1b, includes a metering chamber (12), defined in part by an inner valve body (13), through which a valve stem (14) passes. The valve stem, which is biased outwardly by a compression spring (15), is in sliding sealing engagement with an inner tank seal (16) and an outer diaphragm seal (17). The valve also includes a second valve body (20) in the form of a bottle emptier.

(For the sake of clarity in the description of various metered dose valves, in particular those including at least two valve bodies, in the following a valve body defining in part the metering chamber will be referred to as a "primary" valve body, while other types of valve body, e.g. defining a pre-metering region, a pre-metering chamber, a spring cage and/or a bottle emptier will be referred to as a "secondary" valve body.)

Returning to FIG. 1a, aerosol formulation (4) can pass from the formulation chamber into a pre-metering chamber (22) provided between the secondary valve body (20) and the primary valve body (13) through an annular space (21) between the flange (23) of the secondary valve body and the primary valve body. To actuate (fire) the valve, the valve stem (14) is pushed inwardly relative to the container from its resting position shown in FIGS. 1a and b, allowing formulation to pass from the metering chamber through a side hole (19) in the valve stem and through a stem outlet (24) to an actuator nozzle (7) then out to the patient. When the valve stem (14) is released, formulation enters into the valve, in particular into the pre-metering chamber (22), through the annular space (21) and thence from the pre-metering chamber through a groove (18) in the valve stem past the tank seal (16) into the metering chamber (12).

As mentioned above, FIGS. 2 to 5 show other known metered dose valves used in pMDIs. Similar to the valve shown in FIG. 1, the valves of FIGS. 2 to 5 are typically fitted via a ferrule onto an aerosol container whereby a formulation chamber is defined by the inner walls of the container and the outer walls of the portion(s) of the valve located within the container. For the sake of ease in understanding and comparison, similar components of the respective valves are identified with like reference numbers in the Figures.

Figure 2:
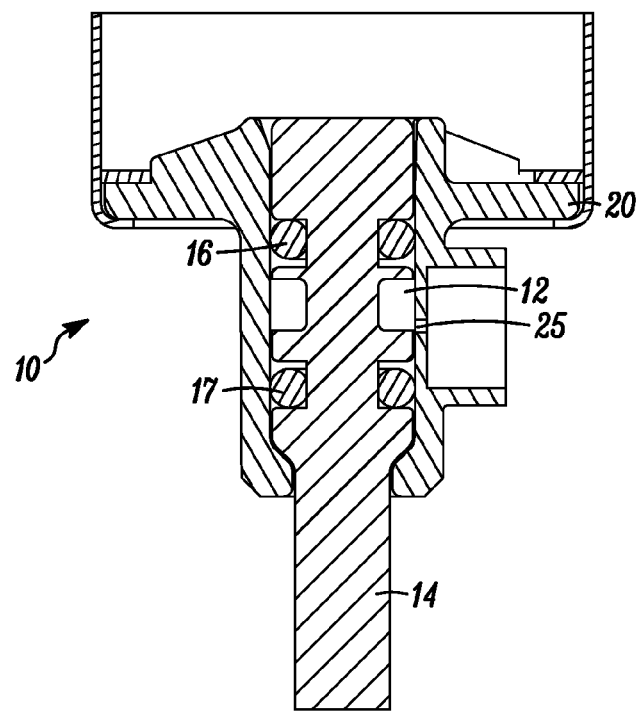
FIGS. 2 to 5 represent schematic cross-sectional views of further metered dose valves known in the art for use in pressurized metered dose inhalers.

FIG. 2 shows a metered dose valve (10) of a type generally similar to that disclosed and described in U.S. Pat. No. 5,772,085 (incorporated herein by reference). The valve is shown in its resting position and includes a valve body (20) and a valve stem (14). The valve stem, which is biased outwardly under the pressure of the aerosol formulation contained within the formulation container, is provided with an inner seal and an outer seal (16 and 17). Unlike the valves in FIG. 1 and FIGS. 3 to 5, which are push-to-fire type valves, the valve here is a release-to-fire type valve. To actuate the valve, the valve stem (14) is first pushed upwards into the formulation chamber (not shown), so that the outer seal (17) passes inwardly beyond an outlet (25) provided in the external portion of the valve body and the inner seal (16) then passes inwardly and disengages from the inner walls of the valve body, thus bringing the metering chamber (12) up into the formulation chamber so that formulation can enter the metering chamber (referred to as the priming position of the valve) and then the valve stem is released moving outwardly so that the inner seal re-engages the valve body and the outer seal then passes outwardly beyond the outlet, bringing the metering chamber in communication with the outlet, so that formulation passes through the outlet to the patient.

Figure 3:
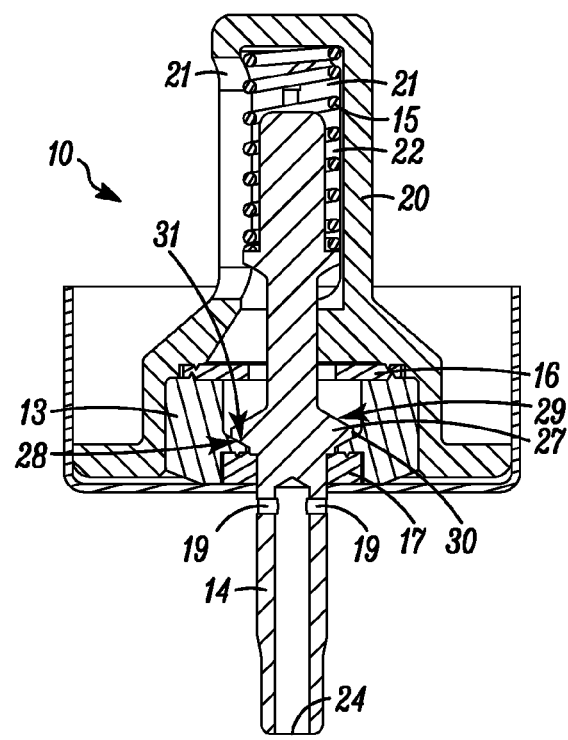

FIG. 3 shows a metered dose valve (10) of the type generally similar to that disclosed and described in WO 2004/022142 (incorporated herein by reference). The valve is shown in its resting position and includes a secondary valve body (20) and a valve stem (14) that is biased outwardly by a compression spring (15). The valve is provided with an inner seal (16) and outer diaphragm seal (17), with the valve stem being in sliding sealing engagement with the diaphragm seal. In this valve, the secondary valve body is in the form of a spring cage housing having three slots (21, two visible) providing communication between the formulation chamber (not shown) and a pre-metering chamber (22). This valve includes a transitory metering chamber formed upon actuation of the valve. During actuation of the valve, as the valve stem (14) is pushed inwardly relative to the container, a metering chamber (12, not visible) is formed between a lower surface (28) of a conical portion (27) of the valve stem (14) and an upper, sloping surface (31) of a primary valve body (13). Aerosol formulation passes around the shoulder (30) of the conical portion of the valve stem into the forming metering chamber and as the valve stem is further pushed in the upper surface (29) of the conical portion forms a face seal with the inner seal (16), thereby sealing off the metering chamber. As the valve stem is yet further displaced inwardly, formulation is allowed to pass from the metering chamber through side holes (19) in the valve stem and through a stem outlet (24) in the valve stem, and subsequently out to the patient typically via an actuator nozzle (7, not shown).

Figure 4:
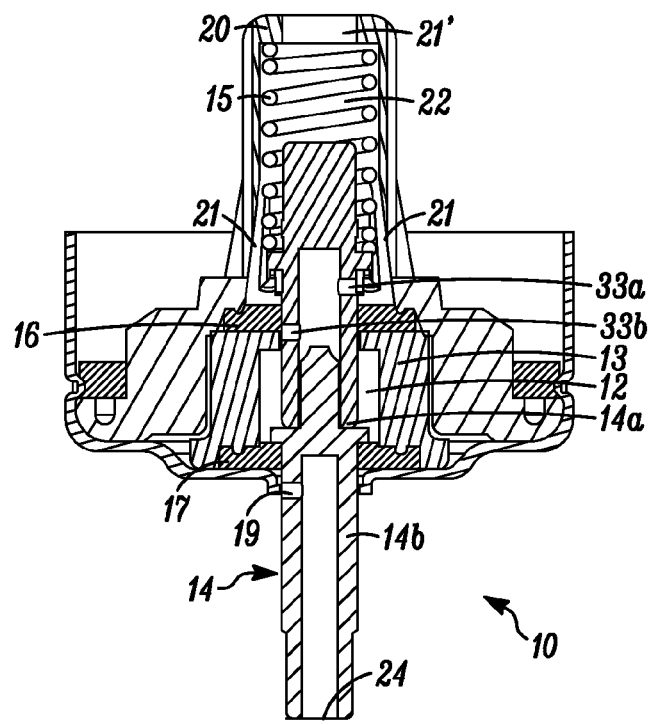

FIG. 4 shows a commercial metered dose valve supplied by Bespak, Bergen Way, King's Lynn, Norfolk, PE30 2JJ, UK under the trade designation BK357, in its resting position. The valve includes a secondary valve body (20) in the form of a spring cage with two slots (21) and an opening at the top (21') allowing communication between the formulation chamber (not shown) and a pre-metering chamber (22). The valve also includes a valve stem (14), made of two components (14a, 14b), which is biased outwardly by a compression spring (15) and passes through a metering chamber (12) defined in part by a primary valve body (13). The valve stem is in sliding sealing engagement with an inner seal (16) and an outer diaphragm seal (17). Aerosol formulation can pass from the pre-metering chamber (22) into the metering chamber (12) via side holes (33a, 33b) in the upper portion (14a) of the stem (14). Similar to the valve shown in FIG. 1, to actuate (fire) the valve, the valve stem (14) is pushed inwardly relative to the container, allowing a metered dose of formulation to pass from the metering chamber through a side hole (19) in the valve stem and through a stem outlet (24) and then typically through an actuator nozzle (7, not shown) out to the patient.

Figure 5:
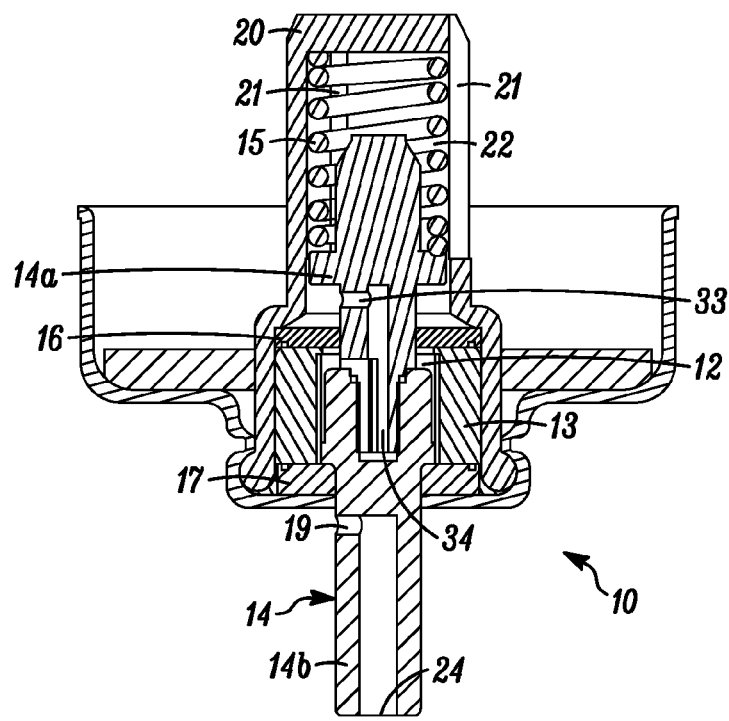

FIG. 5 shows a commercial metered dose valve supplied by Valois SAS, Pharmaceutical Division, Route des Falaises, 27100 le Vaudreuil, France under the trade designation RCS, in its resting position. The valve includes a secondary valve body (20) in the form of a spring cage with three slots (21, two visible) allowing communication between the formulation chamber (not shown) and a pre-metering chamber (22). The valve also include a valve stem (14), made of two components (14a, 14b), which is biased outwardly by a compression spring (15) and passes through a metering chamber (12) defined in part by a primary valve body (13). The valve stem is in sliding sealing engagement with an inner seal (16) and an outer diaphragm seal (17). Aerosol formulation can pass from the pre-metering chamber (22) into the metering chamber through a side hole (33) and an internal channel (34) provided in the upper portion (14a) of the valve stem. Similar to the valve shown in FIG. 1, to actuate (fire) the valve, the valve stem (14) is pushed inwardly relative to the container, allowing formulation to pass from the metering chamber through a side hole (19) in the valve stem and through a stem outlet (24) and then typically through an actuator nozzle (7, not shown) out to the patient.

With the exception of the elastomeric seals used in metered dose valves, typically the components of such valves are made of metal (e.g. stainless steel, aluminum or aluminum alloy) or plastic. For example compression springs are generally made of a metal, in particular stainless steel as the conventional material. Compression springs may also be made of aluminum or aluminum alloy. Valve stems and valve bodies are generally made of metal and/or plastic; as a metal conventionally stainless steel is used (other metals that may be used include aluminum, aluminum alloy and titanium) and as plastics conventionally polybutylene terephthalate (PBT) and/or acetal are used (other polymers that may be used include polyetheretherketones, nylon, other polyesters (such as tetrabutylene terephthalate), polycarbonates and polyethylene).

Favorably at least a portion of a surface, more favorably the entire surface, of a component or components of a medicinal inhalation device (e.g. aerosol containers, actuators, ferrules, valve bodies, valve stems or compression springs of metered dose inhalers or powder containers of dry powder inhalers) which is or will come in contact with a medicament or a medicinal formulation during storage or delivery from the medicinal inhalation device are treated according to methods described herein. Most favorably the entire surface of the component, including any surface or surfaces (if present) that do not or will not come in contact with a medicament or a medicinal formulation during storage or delivery from the device, are treated according to methods described herein. Alternatively or additionally, favorably at least a portion of a surface, more favorably the entire surface, of a component or components of a medicinal inhalation device, which either come in contact with a movable component or are movable during storage or delivery from the medicinal inhalation device are treated according to methods described herein. Examples of such components for metered dose inhalers include e.g. valve bodies, valve stems or compression springs of metered dose valves.

In particular a component of a medicinal inhalation device in accordance with the present invention or made according to methods in accordance with the present invention is a component of a metered dose inhaler. Said component may be selected from the group consisting of aerosol container, an actuator, a ferrule, a valve body (e.g. a primary and/or a secondary valve body), a valve stem and a compression spring. Alternatively a component of a medicinal inhalation device in accordance with the present invention or made according to methods in accordance with the present invention is a component of a dry powder inhaler. Said component may be selected from the group consisting of a component that defines at least in part a powder container (e.g. a multi-dose reservoir container or single dose blister or capsule), an component used to open a sealed powder container (e.g. piercer to open single dose blisters or capsules), a component that defines at least in part a deagglomeration chamber, a component of a deaglomeration system, a component that defines at least in part a flow channel, a dose-transporting component (e.g. a dosing rod, dosing wheel or dosing cylinder with a recess dimensioned to accommodate a single dose of powder trapped between said component and a housing in which it moves to transport the dose), a component that defines at least in part a mixing chamber, a component that defines at least in part an actuation chamber (e.g. a holding chamber where a dose is dispensed prior to inhalation), a mouthpiece and a nosepiece.

Embodiments in accordance with certain aspects of the present invention include forming a non-metal coating on at least a portion of a surface of a medicinal inhalation device or a component of a medicinal inhalation device (e.g. an aerosol container of a metered dose inhaler, a metered dose valve or a component thereof, or a powder container of a dry powder inhaler), said coating having at least one functional group, where the at least one functional group is capable of forming a covalent bond with the at least one functional group of the at least partially fluorinated compound.

The term "at least one functional group" as used herein is to be generally understood to include as a preferred embodiment "a plurality of functional groups".

The at least one functional group of the non-metal coating desirably includes an active hydrogen. The at least one functional group is favorably a hydroxyl group (—OH), a thiol group (—SH), an amine group (—NH— or —NH$_2$), a carboxyl group (—COOH), an amide group (—CONH— or —CONH$_2$) or a mixture of such groups; more favorably a hydroxyl group, a carboxyl group or a mixture of such groups; and most favorably a hydroxyl group.

Favorably the aforesaid forming a non-metal coating includes forming a coating comprising silicon, oxygen, and hydrogen, more favorably a non-metal coating comprising carbon, silicon, oxygen and hydrogen.

Non-metal coatings described herein may be formed through a variety of known coating techniques. However it has been found that the application of such coatings through plasma deposition is desirable, more desirably through plasma deposition under conditions of ion bombardment.

In particular non-metal coatings (more particularly coatings comprising silicon, oxygen and hydrogen, and most particularly coatings comprising silicon, oxygen, hydrogen and carbon) may be desirably provided by plasma polymerization of an appropriate monomer or monomers, optionally in the presence of an appropriate assist gas, such as oxygen, using conventional conditions used in e.g. microwave, inductively coupled, DC and RF (radio frequency) plasma deposition, where polymerized species formed in the plasma deposit on the substrate to provide a polymer coating on the surface(s) of the substrate.

More desirably non-metal coatings (more particularly coatings comprising silicon, oxygen and hydrogen, and most particularly coatings comprising carbon, silicon, oxygen, and hydrogen) are provided by plasma deposition under conditions of ion bombardment. Here plasma deposition is carried out in such a way that an ion sheath is formed upon generation of the plasma (plasma formed from an appropriate source compound or compounds, optionally in the presence of an appropriate assist gas, such as oxygen) and where the substrate, whose surface is or surfaces are to be coated, is positioned within the plasma chamber so that during plasma deposition the substrate is within the ion sheath. An explanation of the formation of ion sheaths can be found in Brian Chapman, Glow Discharge Processes, 153 (John Wily & Sons, New York 1980). For RF-plasma deposition, this can be generally accomplished through the use of a RF-powered electrode and locating the substrate to be coated in proximity to the RF-powered electrode. For microwave plasma deposition and inductively coupled plasma deposition, this can be accomplished by providing the microwave or inductively coupled plasma system, respectively, with an electrode, biasing (generally negatively biasing) this electrode and locating the substrate in proximity to said biased electrode. For DC plasma deposition, this can be accomplished by locating the substrate in proximity to the cathode or negatively biased electrode (e.g. for providing thin coatings of 10 nm or less). In this manner plasma deposition occurs under conditions of ion bombardment. Moreover polymerized species formed in the plasma are subjected to ion bombardment, and are thus among other things fragmented, before depositing and/or upon deposition on the substrate allowing the provision of an advantageous, dense, random, covalent system on the surface(s) of the substrate. Such amorphous covalent systems (in particular such systems comprising silicon, oxygen and hydrogen, and more particularly further comprising carbon), show excellent adhesion (through e.g. covalent bonding) to many substrate materials, including metals, polymers, glass and ceramics. Such covalent amorphous systems provide "sharp" coatings e.g. on complex-formed components such as valve stems or compression springs. Such covalent amorphous systems (in particular such systems comprising silicon, oxygen and hydrogen, and more particularly further comprising carbon) are desirable in that they are typically transparent or translucent. Furthermore, such amorphous covalent systems show advantageously high atomic packing densities, typically in a range from about 0.20 to about 0.28 (in particular from about 0.22 to about 026) gram atom number density in units of gram atoms per cubic centimeter. Polymeric coatings (e.g. plasma polymer coatings) generally have gram atom number densities around 0.18. Such high atomic packing densities allow the provision of coatings having a minimum of porosity, excellent resistance to diffusion to liquid or gaseous materials, and superb, "diamond-like" hardness. Micro-hardness of such coatings, as determined using a nanoidenter, is generally, favorably at least 1 GPa, more favorably at least 2 GPa. Such coatings also advantageously have a low coefficient of friction/surface energy. Such coatings further comprising carbon, generally termed here as "diamond-like glass" show desirous flexibility together with diamond-like hardness, allowing for desirable long-term durability, in particular advantageous long-term durability of said coatings on movable components (e.g. compression springs) or on components coming into contact with other components due to movement (e.g. valve stems, valve bodies). Micro-elastic-modulus of such coatings, as determined using a nanoidenter, is generally, favorably at least 11 GPa, more favorably at least 13 GPa. Due to the desirable properties of the aforesaid described coatings, they are particularly advantageous for use as coatings in medicinal inhalation devices or components thereof either alone or as a coating onto which a composition comprising an at least partially fluorinated compound comprising at least one functional group is applied. In regard to the latter, again due to desirable high atomic packing densities such non-metal coatings allow for the provision of a dense distribution and high number of functional groups, such as functional groups having an active hydrogen (e.g. hydroxyl groups (—OH) and/or carboxyl groups (—COOH), in particular hydroxyl groups) for subsequent bonding upon application of said composition comprising at least partially fluorinated compound comprising an at least one functional group.

Coatings provided by plasma deposition under conditions of ion bombardment and comprising silicon, oxygen and hydrogen desirably have a silicon to oxygen ratio less than two.

Diamond-like glass coatings (e.g. coatings provided by plasma deposition under conditions of ion bombardment and comprising carbon, silicon, oxygen and hydrogen) favorably contain on a hydrogen free basis at least about 20 atomic percent carbon and at least about 30 atomic percent of silicon+oxygen, more favorably at least about 25 atomic percent carbon, about 15 to about 50 atomic percent of silicon and about 15 to about 50 atomic percent oxygen, even more favorably about 30 to about 60 atomic percent carbon, about 20 to about 45 atomic percent of silicon and about 20 to about 45 atomic percent oxygen, yet even more favorably about 30 to about 50 atomic percent carbon, about 25 to about 35 atomic percent of silicon and about 25 to about 45 atomic percent oxygen, and most favorably about 30 to about 36 atomic percent carbon, about 26 to about 32 atomic percent of silicon and about 35 to about 41 atomic percent oxygen. Diamond-like glass coatings desirably have a silicon to oxygen ratio less than two. "Hydrogen free basis" refers to the atomic composition of a material as established by a method such as Electron Spectroscopy for Chemical Analysis (ESCA) which does not detect hydrogen even if large amounts are present in the coating. The combination of fairly high amounts of silicon and oxygen with significant amounts carbon makes diamond-like glass coatings flexible (unlike glass or amorphous carbon coatings such as diamond-like carbon coatings). Also due to said combination diamond-like glass coatings have relatively low intrinsic stress and thus excellent long-term adhesion and durability (unlike diamond-like carbon coatings which have a tendency to flake off due to relatively high intrinsic stress within the coating). Thus diamond like glass coatings are particularly advantageous as coatings on a surface or surfaces of medicinal inhalation device components which undergo movement in itself (e.g. a compression spring of a metered dose valve) or movement in conjunction with or relative to other components (e.g. a valve stem of a metered dose valve). Diamond-like glass coatings as well as methods of making diamond-like glass and apparatus for depositing diamond-like glass are described in U.S. Pat. No. 6,696,157 (David et al), the contents of which is incorporated here in its entirety.

It is to be recognized that plasma deposition under conditions of ion bombardment is distinct from plasma polymerization. Moreover in plasma polymerization techniques, plasma deposition is carried out in such a manner that no ion sheath is formed (e.g. using conventional microwave or inductively coupled plasma systems) or the substrate to be coated with the polymer is positioned outside of any ion sheath, if at all formed. For example, in regard to the RF-plasma systems using a RF-powered electrode, for plasma polymerization, i.e. deposition of the polymer on the substrate, the substrate is located in proximity to the grounded electrode or placed at a floating potential (i.e. electrically isolated and located outside of any ion sheath formed during RF-plasma deposition).

The term "plasma deposition" as used herein, unless otherwise specified, will be understood to include inter alia plasma polymerization as well as plasma deposition under conditions of ion bombardment, where in each case plasma deposition under conditions of ion bombardment is understood to be preferred. Similarly the term "plasma deposited" as used herein, unless otherwise specified, will be understood to include inter alia plasma polymerized as well as plasma deposited under ion bombardment, where in each case plasma deposited under ion bombardment is understood to be preferred.

Figure 6:
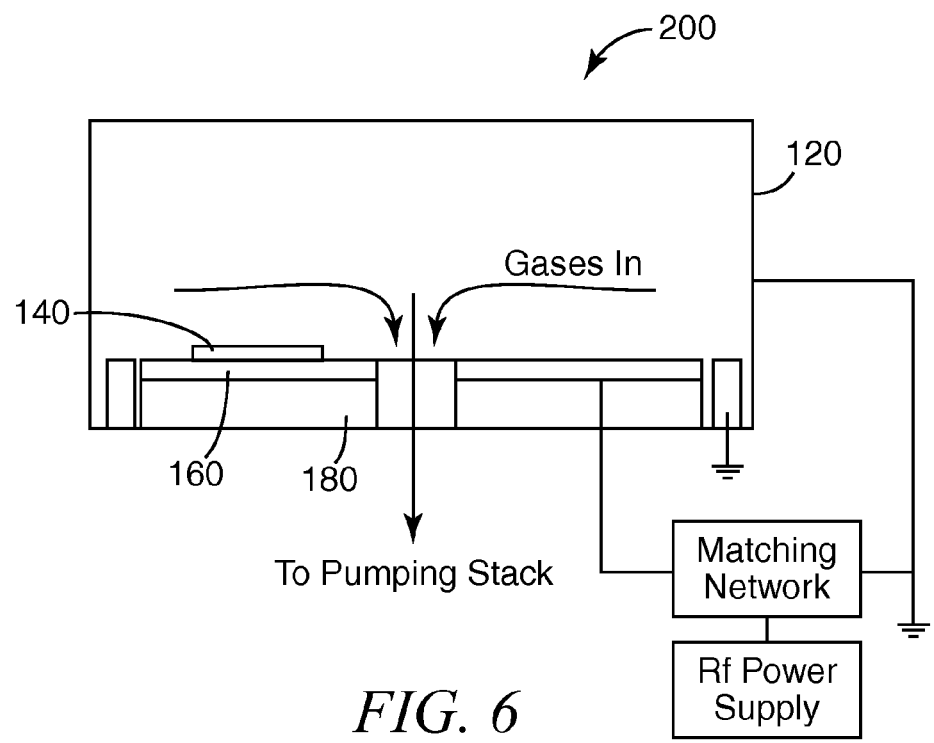
FIGS. 6 and 7 each show a schematic cross-section of an exemplary apparatus suitable for plasma depositing, in particular under conditions of ion bombardment, a non-metal coating on at least a portion of the surface of a substrate (e.g. a component of a medicinal inhalation device).
Figure 7:
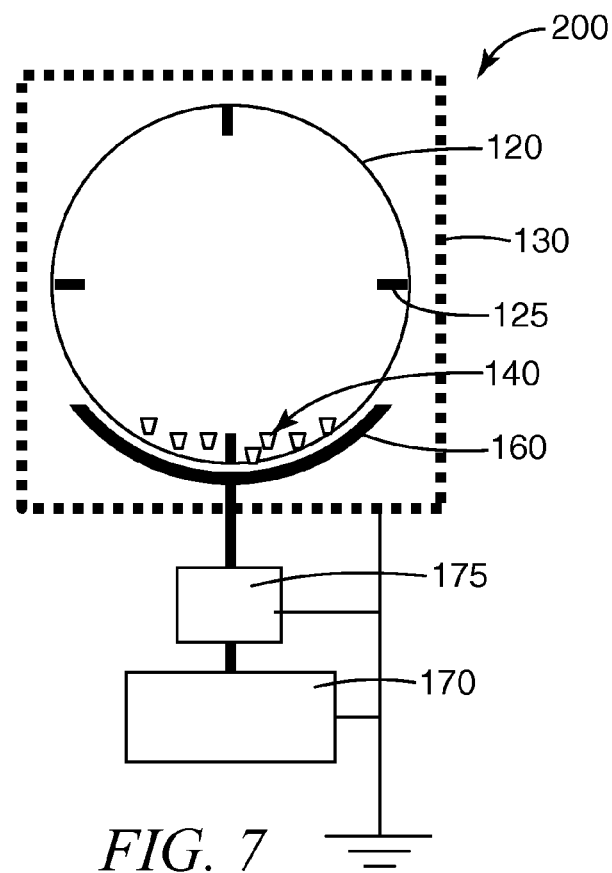

Forming a non-metal coating as described herein by plasma deposition can be carried out in a suitable reaction chamber having a capacitively-coupled system with at least one electrode powered by an RF (radio frequency) source and at least one grounded electrode, such as those described in U.S. Pat. Nos. 6,696,157 (David et al.) and 6,878,419 (David et al.). FIG. 6 illustrates an exemplary apparatus (200) suitable for the plasma deposition, in particular plasma deposition under conditions of ion bombardment, showing a grounded chamber (120) (also acting here as a grounded electrode) from which air is removed by a pumping stack (not shown). The gas or gases to form the plasma are generally injected radially inwardly through the reactor wall to an exit pumping port in the center of the chamber. Substrate (140), typically a medicinal inhalation device component per se or alternatively a work-piece from which such a component may be subsequently formed or worked, is favorably positioned proximate RF-powered electrode (160). Electrode (160) is insulated from chamber (120) by a polytetrafluoroethylene support (180). FIG. 7 illustrates another exemplary apparatus (200) for the plasma deposition, in particular plasma deposition under conditions of ion bombardment, where a substrate or (as shown in FIG. 7) a plurality of substrates (140) (again such substrate(s) being typically medicinal inhalation device component(s) per se or alternatively a work-piece(s) from which such a component may be subsequently formed or worked) are tumbled during deposition, such tumbling favorably allowing for uniform deposition on the surfaces of the substrate(s). Here the chamber (120) is a tube, in particular a quartz tube, the ends of which are sealed with flanges (not shown), in particular aluminum flanges. Each end flange is typically provided with a port, a port at one end being connected to a pumping stack (not shown) and a port at the other end being connected to gas supply system (not shown). The ports together with the connecting-system are favorably configured and arranged to allow for rotation of the tube and thus the chamber during plasma deposition. Air is typically removed from the chamber after loading by the pumping stack through the exit pumping port, and the gas or gases to form the plasma are generally injected through the inlet gas port at the other end, said gas or gases passing then through the chamber towards the exit pumping port. RF-powdered electrode (160) is advantageously configured as an arc conforming to the curvature of the tube and is positioned just underneath the tube but separated from the tube by a narrow gap. The chamber and RF-powered electrode are favorably housed inside with a housing (130), in particular a housing made of a perforated metal, that serves as a grounded counter electrode. Similar to the system shown in FIG. 6, power is typically provided by a RF power supply (170) through a matching network (175). During treatment with such a system, the chamber (120) is advantageously rotated so the substrate(s) (140) to be coated tumble; tumbling can be desirably facilitated through the inclusion of baffles (125) within the tube. Through an appropriate degree of substrate loading together with tumbling at an appropriate rate during plasma deposition, the substrate(s) to be coated will be found with the lower portion of the tube, and thus favorably positioned in proximity of the RF-powered electrode (160) so that the substrate(s) will be located within the ion sheath.

Before plasma deposition, it is desirable to expose the substrate to an oxygen plasma or alternatively an argon plasma, more desirably oxygen plasma. It is most desirable to expose the substrate to an oxygen plasma under conditions of ion bombardment (i.e. generating an ion sheath and having the substrate located within the ion sheath during said oxygen plasma treatment). Typically for this pre-treatment, pressures in the chamber are maintained between 1.3 Pa (10 mTorr) and 27 Pa (200 mTorr). Plasma is generated with RF power levels of between 500 W and 3000 W.

A solvent washing step with an organic solvent such as acetone or ethanol may also be included prior to the exposure to an oxygen or argon plasma as described above.

Referring to the exemplary apparatus shown in FIG. 6, for plasma deposition under ion bombardment conditions the substrate is located in proximity of the RF-powered electrode (as schematically depicted in FIG. 6) in the chamber so that the substrate will be within the ion sheath. For plasma polymerization, the substrate to be coated would be placed in the chamber at a floating potential with the substrate being located such that it would not be within the ion sheath. Alternatively for plasma polymerization, an alternative system may be used which is provided with an additional grounded electrode (rather than having the chamber act as the grounded electrode) and the substrate to be coated would be then located in the proximity of the grounded electrode.

The chamber is typically evacuated to the extent necessary to remove air and any impurities. This may be accomplished by vacuum pumps at a pumping stack connected to the chamber. A source gas is introduced into the chamber at a desired flow rate, which depends on the size of the reactor, the surface area of the electrodes, and the surface area of the substrate. The gas is typically and desirably oxygen.

For the provision of a plasma deposited coating comprising silicon, oxygen and hydrogen or a plasma deposited coating comprising carbon, silicon, oxygen and hydrogen, during plasma deposition, the gas further comprises an appropriate organosilicon and/or a silicon hydride compound, and the flow rates are sufficient to establish a suitable pressure at which to carry out plasma deposition, typically 0.13 Pa to 130 Pa (0.001 Torr to 1.0 Ton). For a cylindrical reactor that has an inner diameter of approximately 55 cm and a height of approximately 20 cm, the flow rates are typically from about 50 to about 500 standard cubic centimeters per minute (sccm). At the pressures and temperatures (less than about 50° C.) of the plasma deposition, the gas remains in the vapor form. An RF electric field is applied to the powered electrode, ionizing the gas and establishing a plasma. In the RF-generated plasma, energy is coupled into the plasma through electrons. The plasma acts as the charge carrier between the electrodes. The plasma can fill the entire reaction chamber and is typically visible as a colored cloud.

The plasma also forms an ion sheath proximate at least to the RF-powered electrode. The ion sheath typically appears as a darker area around the electrode. The depth of the ion sheath normally ranges from about 1 mm to about 50 mm and depends on factors such as the type and concentration of gas used, pressure in the chamber, the spacing between the electrodes, and relative size of the electrodes. For example, reduced pressures will increase the size of the ion sheath. When the electrodes are different sizes, a larger, stronger ion sheath will form around the smaller electrode. Generally, the larger the difference in electrode size, the larger the difference in the size of the ion sheaths, and increasing the voltage across the ion sheath will increase ion bombardment energy.

In preferred embodiments in which a substrate, whose surface is or surfaces are to be coated, is located within an ion sheath, ions accelerating toward the electrode bombard the species being deposited from the plasma onto the substrate and thus the substrate is exposed to the ion bombarded species being deposited from the plasma. The resulting reactive species within the plasma react on the surface of the substrate, forming a coating, the composition of which is controlled by the composition of the gas being ionized in the plasma. The species forming the coating are advantageously attached to the surface of the substrate by covalent bonds, and therefore the coating is advantageously covalently bonded to the substrate.

For favorable embodiments including formation of a coating comprising silicon, oxygen, and hydrogen or more favorably a coating comprising carbon, silicon, oxygen and hydrogen, plasma deposition comprises ionizing a gas comprising at least one of an organosilicon or a silicon hydride compound. Typically the silicon of the at least one of an organosilicon or a silicon hydride compound is present in an amount of at least about 5 atomic percent of the gas mixture. If a reactive gas (such as oxygen) and/or an inert gas (such as argon) are mixed along with the organosilicon and/or silicon hydride source compound, the atomic percent of silicon in the gas mixture is calculated based on the volumetric (or molar) flow rates of the component gases in the mixture. For embodiments including formation of a coating comprising carbon, silicon, oxygen and hydrogen, the gas desirably comprise an organosilicon. In particular the organosilicon comprises at least one of trimethylsilane, triethylsilane, trimethoxysilane, triethoxysilane, tetramethylsilane, tetraethylsilane, tetramethoxysilane, tetraethoxysilane, hexamethylcyclotrisiloxane, tetramethylcyclotetrasiloxane, tetraethylcyclotetrasiloxane, octamethylcyclotetrasiloxane, hexamethyldisiloxane, and bistrimethylsilylmethane. More particularly the organosilicon comprises at least one of trimethylsilane, triethylsilane, tetramethylsilane, tetraethylsilane, and bistrimethylsilylmethane; and most particularly the organosilicon comprises tetramethylsilane. In addition to or alternatively (e.g. for provision of coatings comprising silicon, oxygen and hydrogen having less than 20 atomic percent of carbon (on hydrogen-free basis) or no carbon), the gas may comprise a silicon hydride. The silicon hydride may comprise $SiH_4$ (silicon tetrahydride) and/or $Si_2H_6$ (disilane), in particular $SiH_4$ (silicon tetrahydride).

Preferably the gas further comprises oxygen.

The gas may further comprise an additional gas or gases. Each additional gas can be added separately or in combination with each other. The gas may further comprise argon and/or hydrogen, in particular for plasma deposition under ion bombardment conditions. The application of argon (normally is not incorporated into the deposited coating) enhances ion bombardment, while the application of hydrogen promotes the formation of high packing density as well as provides an additional source of hydrogen. Optionally the gas may further comprise ammonia and/or nitrogen. However for certain preferred embodiments, described in more detailed infra, in which a composition comprising an at least partially fluorinated compound comprising at least one silane group will be applied, it is desirable not to use ammonia and nitrogen gas, nor a sulfur containing gas. Moreover, for certain preferred embodiments in which a composition comprising an at least partially fluorinated compound comprising at least one silane group will be applied, it is desirable that the non-metal coating as described herein is substantially free or free of amine groups and substantially free or free of amido groups as well as substantially free or free of thiol groups so as to minimize or avoid formation of silicon-nitrogen or silicon-sulfur bonds, said bonds having been determined to be undesirable in terms of durability and/or robustness of the coating system over the life of medicinal inhalation devices. Accordingly in preferred embodiments, the non-metal coating is advantageously substantially free of nitrogen (e.g. at most about 5 atomic percent of nitrogen (on a hydrogen free basis)), in particular free of nitrogen. Also in preferred embodiments, the non-metal coating is advantageously substantially free of sulfur (e.g. at most about 1 atomic percent of sulfur (on a hydrogen free basis)), in particular free of sulfur. Optionally the gas may further comprise a source of fluorine e.g. carbon tetrafluoride. However, it is preferred (in general and more particularly for plasma deposition under ion bombardment conditions) not to include fluorine into the non-metal coating. The inclusion of fluorine has been determined to be generally undesirable in terms of structural integrity of non-metal coating (in particular adhesion of the non-metal coating to the substrate surface as well as overall durability of the non-metal coating). Also for those embodiments in which a composition comprising an at least partially fluorinated compound comprising at least one functional group is applied onto the non-metal coating the inclusion of fluorine is undesirable in terms of adhesion of the applied fluorine-containing composition onto the non-metal coating. Thus in certain aspects of the present invention and in preferred embodiments of other aspects of the present invention, the non-metal coating is advantageously substantially free of fluorine (e.g. at most about 1 atomic percent of fluorine (on a hydrogen free basis)), in particular free of fluorine.

Plasma deposition of the non-metal coating typically occurs at a rate ranging from about 1 to about 100 nm/second. The rate will depend on conditions including pressure, power, concentration of gas, types of gases, relative size of the electrodes, and so on. In general, the deposition rate increases with increasing power, pressure, and concentration of gas, although the rate can approach an upper limit.

Desirably plasma deposition of the non-metal coating is carried out for a period of time such that the coating has a thickness in the range from about 5 nm to about 5000 nm. Generally within this range it is favorable to provide coatings having a thickness of at least about 10 nm, more favorably at least about 50 nm, and most favorably at least about 100 nm. Also within the aforesaid ranges generally it is favorable to provide coatings having a thickness less than about 1000 nm, more favorably at most about 950 nm, even more favorably at most about 800 nm, yet even more favorably at most about 675 nm and most favorably at most about 550 nm.

After the non-metal coating is formed (in particular a non-metal coating comprising silicon, oxygen and hydrogen, more particularly a coating comprising carbon, silicon, oxygen, hydrogen formed by plasma deposition) the surface of the non-metal coating is favorably exposed to an oxygen plasma, more favorably exposed to an oxygen plasma under ion bombardment conditions (for example in order to form or to form additional silanol groups on the surface of the non-metal coating). Such a treatment is particularly advantageous for embodiments in which a composition comprising an at least partially fluorinated compound comprising at least one functional group will be applied. For such treatment, pressures in the plasma chamber are typically maintained between 1.3 Pa (10 mTorr) and 27 Pa (200 mTorr), and oxygen plasma is generated with RF power levels of between about 50 W and about 3000 W.

Embodiments according to certain aspects of the present invention include applying to at least a portion of a surface of the non-metal coating a composition comprising an at least partially fluorinated compound comprising at least one functional group, and allowing at least one functional group of the at least partially fluorinated compound to react with at least one functional group of the non-metal coating to form a covalent bond. Preferably said composition is applied to the entire surface of the non-metal coating.

As mentioned previously, prior to applying the composition comprising an at least partially fluorinated compound comprising at least one functional group, the non-metal coating is desirably exposed to an oxygen plasma, more desirably exposed to an oxygen plasma under ion bombardment conditions. Alternatively, the non-metal coating may be favorably exposed to a corona treatment prior to applying the composition comprising the at least partially fluorinated compound comprising at least one functional group.

Desirably the at least partially fluorinated compound includes a polyfluoropolyether segment, preferably a perfluorinated polyfluoropolyether segment, for enhanced surface properties as well as enhanced coating efficiency and structural integrity. The use of polyfluoropolyether segments including perfluorinated repeating units including short chains of carbon, where desirably the number of carbon atoms in sequence is at most 6, more desirably at most 4, even more desirably at most 3, and most desirably at most 2, facilitates durability/flexibility of the applied fluorine-containing coating as well as minimizing a potential of bioaccumulation of perfluorinated moieties.

Desirably the at least one functional group of the at least partially fluorinated compound includes a hydrolysable group (e.g. hydrolysable in the presence of water, optionally under acidic or basic conditions producing groups capable of undergoing a condensation reaction (for example silanol groups)).

Desirably the at least one functional group of the at least partially fluorinated compound is a silane group.

Favorably the silane group includes at least one hydrolysable group, more favorably at least two hydrolysable groups, and most favorably three hydrolysable groups. The hydrolysable groups may be the same or different.

Desirably a hydrolysable group is a group selected from the group consisting of hydrogen, halogen, alkoxy, acyloxy, aryloxy, and polyalkyleneoxy, more desirably a group selected from the group consisting of alkoxy, acyloxy, aryloxy, and polyalkyleneoxy, even more desirably a group selected from the group consisting of alkoxy, acyloxy and aryloxy, and most desirably an alkoxy group (e.g. OR' wherein each R' is independently a $C_{1-6}$ alkyl, in particular a $C_{1-4}$ alkyl).

Desirably the at least partially fluorinated compound comprising at least one functional group is a polyfluoropolyether silane, more desirably a multifunctional polyfluoropolyether silane, and most desirably a difunctional polyfluoropolyethersilane.

The term "multifunctional polyfluoropolyether silane" as used herein is generally understood to mean a multivalent polyfluoropolyether segment functionalized with a multiple of functional silane groups, and the term "difunctional polyfluoropolyether silane" as used herein is generally understood to mean a divalent polyfluoropolyether segment functionalized with a multiple of functional silane groups (in particular two to four functional silane groups, more particular two functional silane groups).

It has been found that the use of a multifunctional polyfluoropolyether silane, in particular a difunctional polyfluoropolyether silane, allows for high application efficiency and coverage as well as extensive bonding (covalent bonding) to the non-metal coating and cross-linking within the fluorine containing coating itself facilitating structural integrity of the applied fluorine-containing coating.

For enhanced stability and/or resistance to attack (e.g. by ethanol, drug, and/or other potential components of medicinal inhalation formulations) desirably polyfluoropolyether segment(s) is (are) not linked to silane group(s) via a functionality that includes a nitrogen-silicon bond or sulfur-silicon bond. In particular, for enhanced stability and resistance of the applied fluorine-containing coating to attack, it is desirable that polyfluoropolyether segment(s) is (are) linked to silane group(s) via a functionality that include a carbon-silicon bond, more particularly via a —C(R)$_2$—Si functionality where R is independently hydrogen or a $C_{1-4}$ alkyl group (preferably hydrogen), and most particular, via a —(C(R)$_2$)$_k$—C(R)$_2$—Si functionality where k is at least 2 (preferably 2 to about 25, more preferably 2 to about 15, most preferably 2 to about 10). The inclusion of —(C(R)$_2$)$_k$— where k is at least 2 advantageously, additionally provides flexural strength Favorably, the at least partially fluorinated compound comprising at least one silane group is a polyfluoropolyether silane of the Formula Ia:

$$R_f[Q\text{-}[C(R)_2\text{—}Si(Y)_{3-x}(R^{1a})_x]_y]_z \qquad \text{Ia}$$

wherein:
$R_f$ is a monovalent or multivalent polyfluoropolyether segment;
Q is an organic divalent or trivalent linking group;
each R is independently hydrogen or a $C_{1-4}$ alkyl group;
each Y is independently a hydrolysable group;
$R^{1a}$ is a $C_{1-8}$ alkyl or phenyl group;
x is 0 or 1 or 2;
y is 1 or 2; and
z is 1, 2, 3, or 4.

Application of polyfluoropolyether silanes in accordance with Formula Ia favorably allows the provision of medicinal inhalation devices or components thereof comprising a non-metal coating on at least a portion of surface of the device or component, as applicable, and a polyfluoropolyether-containing coating bonded to the non-metal coating, wherein the polyfluoropolyether-containing coating comprises polyfluoropolyether silane entities of the following Formula Ib:

$$R_f[Q\text{-}[C(R)_2\text{—}Si(O\text{—})_{3-x}(R^{1a})_x]_y]_z \qquad \text{Ib}$$

which shares at least one covalent bond with non-metal coating; and
wherein:
$R_f$ is a monovalent or multivalent polyfluoropolyether segment;
Q is an organic divalent or trivalent linking group;
each R is independently hydrogen or a $C_{1-4}$ alkyl group;
$R^{1a}$ is a $C_{1-8}$ alkyl or phenyl group;
x is 0 or 1 or 2;
y is 1 or 2; and
z is 1, 2, 3, or 4.

Advantageously the at least one covalent bond shared with the non-metal coating is a bond to an oxygen atom in Si(O—)$_{3-x}$. Favorably such polyfluoropolyether-containing coatings are typically transparent or translucent.

The monovalent or multivalent polyfluoropolyether segment, $R_f$, includes linear, branched, and/or cyclic structures, that may be saturated or unsaturated, and includes two or more in-chain oxygen atoms. $R_f$ is preferably a perfluorinated group (i.e., all C—H bonds are replaced by C—F bonds). However, hydrogen atoms may be present instead of fluorine atoms provided that not more than one atom of hydrogen is present for every two carbon atoms. When hydrogen atoms are present, preferably, $R_f$ includes at least one perfluoromethyl group.

For certain embodiments, the monovalent or multivalent polyfluoropolyether segment, $R_f$, comprises perfluorinated repeating units selected from the group consisting of —(C$_n$F$_{2n}$)—, —(C$_n$F$_{2n}$O)—, —(CF(Z))—, —(CF(Z)O)—, —(CF(Z)C$_n$F$_{2n}$O)—, —(C$_n$F$_{2n}$CF(Z)O)—, —(CF$_2$CF(Z)O)—, and combinations thereof; wherein n is an integer from 1 to 6; Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted. For units comprising Z it is desirable that the total number of carbon atoms in sequence per unit is at most 6 (more desirably at most 4, and most desirably at most 3). Being oligomeric or polymeric in nature, these compounds exist as mixtures and are suitable for use as such. The perfluorinated repeating units may be arranged randomly, in blocks, or in an alternating sequence. Favorably, the polyfluoropolyether segment comprises perfluorinated repeating units selected from the group consisting of —(C$_n$F$_{2n}$O)—, —(CF(Z)O)—, —(CF(Z)C$_n$F$_{2n}$O)—, —(C$_n$F$_{2n}$CF(Z)O)—, —(CF$_2$CF(Z)O)—, and combinations thereof; and more favorably perfluorinated repeating units selected from the group consisting of —$(C_nF_{2n}O)$—, —$(CF(Z)O)$—, and combinations thereof. For certain of these embodiments, n is an integer from 1 to 4; or 1 to 3; or 1 or 2. For certain of these embodiments, Z is a —$CF_3$ group.

For certain embodiments, including any one of the above embodiments, $R_f$ is monovalent, and z is 1. For certain of these embodiments, $R_f$ is terminated with a group selected from the group consisting of $C_nF_{2n+1}$—, $C_nF_{2n+1}O$—, and X'$C_nF_{2n}O$— wherein X' is a hydrogen. For certain of these embodiments, the terminal group is $C_nF_{2n+1}$— or $C_nF_{2n+1}O$— wherein n is an integer from 1 to 6 or 1 to 3. For certain of these embodiments, the approximate average structure of $R_f$ is $C_3F_7O(CF(CF_3)CF_2O)_pCF(CF_3)$—, $CF_3O(C_2F_4O)_pCF_2$—, $C_3F_7O(CF(CF_3)CF_2O)_pCF_2CF_2$—, $C_3F_7O(CF_2CF_2CF_2O)_pCF_2CF_2$—, or $C_3F_7O(CF_2\ CF_2CF_2O)_pCF(CF_3)$—, or $CF_3O(CF_2CF(CF_3)O)_p(CF_2O)X$— (wherein X is $CF_2$—, $C_2F_4$—, $C_3F_6$—, $C_4F_8$—) wherein the average value of p is 3 to 50.

For enhanced application efficiency and coverage as well as extensive bonding to non-metal coating and inter-linking within the fluorine-containing coating itself, thus facilitating a high structural integrity of applied fluorine-containing coating, $R_f$ is preferably multivalent and z is 2, 3 or 4, more preferably $R_f$ is divalent, and z is 2. For certain of these embodiments, the approximate average structure of $R_f$ is selected from the group consisting of —$CF_2O(CF_2O)_m(C_2F_4O)_pCF_2$—, —$CF_2O(C_2F_4O)_pCF_2$—, —$CF(CF_3)O(CF(CF_3)CF_2O)_pCF(CF_3)$—, —$(CF_2)_3O(C_4F_8O)_p(CF_2)_3$—, —$CF(CF_3)$—$(OCF_2CF(CF_3))_pO$—$C_tF_{2t}$—$O(CF(CF_3)CF_2O)_pCF(CF_3)$— (wherein t is 2 to 4), and wherein m is 1 to 50, and p is 3 to 40. For certain of these embodiments, $R_f$ is selected from the group consisting of —$CF_2O(CF_2O)_m(C_2F_4O)_pCF_2$—, —$CF_2O(C_2F_4O)_pCF_2$—, and —$CF(CF_3)$—$(OCF_2CF(CF_3))_pO$—$(C_tF_{2t})$—$O(CF(CF_3)CF_2O)_pCF(CF_3)$—, and wherein t is 2, 3 or 4, and the average value of m+p or p+p or p is from about 4 to about 24.

The above structures are approximate average structures where p and m designate the number of randomly distributed perfluorinated repeating units. Further, polyfluoro-polyether silanes, such as those described above, also typically include a distribution of oligomers and/or polymers, so p and/or m may be non-integral and where the number is the approximate average is over this distribution.

The organic divalent or trivalent linking group, Q, can include linear, branched, or cyclic structures that may be saturated or unsaturated. The organic divalent or trivalent linking group, Q, optionally contains one or more heteroatoms selected from the group consisting of sulfur, oxygen, and nitrogen, and/or optionally contains one or more functional groups selected from the group consisting of esters, amides, sulfonamides, carbonyl, carbonates, ureylenes, and carbamates. Again for flexural strength Q favorably includes a segment with not less than 2 carbon atoms, said segment of Q being directly bonded to the —$C(R)_2$— group of the silane-containing moiety (i.e. for Formula Ia —$C(R)_2$—Si$(Y)_{3-x}(R^{1a})_x$ and for Formula Ib —$C(R)_2$—Si$(O$—$)_{3-x}(R^{1a})_x$). For such embodiments generally Q includes not more than about 25 carbon atoms. Q is preferably substantially stable against hydrolysis and other chemical transformations, such as nucleophilic attack. When more than one Q groups are present, the Q groups can be the same or different.

For certain embodiments, including any one of the above embodiments, Q includes organic linking groups such as —$C(O)N(R)$—$(CH_2)_k$—, —$S(O)_2N(R)$—$(CH_2)_k$—, —$(CH_2)_k$—, —$CH_2O$—$(CH_2)_k$—, —$C(O)S$—$(CH_2)_k$—, —$CH_2OC(O)N(R)$—$(CH_2)_k$—, and

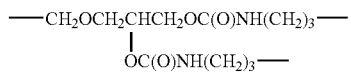

wherein R is hydrogen or $C_{1-4}$ alkyl, and k is 2 to about 25. For certain of these embodiments, k is 2 to about 15 or 2 to about 10.

Favorably Q is a divalent linking group, and y is 1. In particular, Q is favorably a saturated or unsaturated hydrocarbon group including 1 to about 15 carbon atoms and optionally containing 1 to 4 heteroatoms and/or 1 to 4 functional groups. For certain of these embodiments, Q is a linear hydrocarbon containing 1 to about 10 carbon atoms, optionally containing 1 to 4 heteroatoms and/or 1 to 4 functional groups. For certain of these embodiments, Q contains one functional group. For certain of these embodiments, Q is preferably —$C(O)N(R)(CH_2)_2$—, —$OC(O)N(R)(CH_2)_2$—, —$CH_2O(CH_2)_2$—, or —$CH_2$—$OC(O)N(R)$—$(CH_2)_2$—, wherein R is hydrogen or $C_{1-4}$ alkyl.

For certain embodiments, including any one of the above embodiments, where R is present R is hydrogen.

The hydrolyzable groups, Y, of Formula Ia may be the same or different and are capable of hydrolyzing, for example, in the presence of water, optionally under acidic or basic conditions, producing groups capable of undergoing a condensation reaction, for example silanol groups.

Desirably, each Y of Formula Ia is independently a group selected from the group consisting of hydrogen, halogen, alkoxy, acyloxy, aryloxy, and polyalkyleneoxy, more desirably each Y is independently a group selected from the group consisting of alkoxy, acyloxy, aryloxy, and polyalkyleneoxy, even more desirably each Y is independently a group selected from the group consisting of alkoxy, acyloxy and aryloxy, and most desirably each Y is independently an alkoxy group.

For certain embodiments, including any relevant embodiment described herein:

Favorably alkoxy is —OR', and acyloxy is —OC(O)R', wherein each R' is independently a lower alkyl group, optionally substituted by one or more halogen atoms. For certain embodiments, R' is preferably $C_{1-6}$ alkyl and more preferably $C_{1-4}$ alkyl. R' can be a linear or branched alkyl group.

Favorably aryloxy is —OR" wherein R" is aryl optionally substituted by one or more substituents independently selected from halogen atoms and $C_{1-4}$ alkyl optionally substituted by one or more halogen atoms. For certain embodiments, R" is preferably unsubstituted or substituted $C_{6-12}$ aryl and more preferably unsubstituted or substituted $C_{6-10}$ aryl.

Favorably polyalkyleneoxy is —O—$(CHR^4$—$CH_2O)_q$—$R^3$ wherein $R^3$ is $C_{1-4}$ alkyl, $R^4$ is hydrogen or methyl, with at least 70% of $R^4$ being hydrogen, and q is 1 to 40, preferably 2 to 10.

For certain embodiments, including any one of the above embodiments, x is 0.

For certain embodiments, including any one of the above embodiments including a compound in accordance with Formula Ia, $R_f$ is —$CF_2O(CF_2O)_m(C_2F_4O)_pCF_2$— and Q-C(R)$_2$—Si$(Y)_{3-x}(R^{1a})_x$ is C(O)NH$(CH_2)_3$Si(OR')$_3$ wherein R' is methyl or ethyl. For certain embodiments, including any one of the above embodiments including an entity in accordance with Formula Ib, $R_f$ is —$CF_2O(CF_2O)_m(C_2F_4O)_pCF_2$— and Q-C(R)$_2$—Si$(O$—$)_{3-x}(R^{1a})_x$ is C(O)NH$(CH_2)_3$Si(O—)$_3$. For certain of these embodiments, m and p are each about 9 to 12.

The compounds of Formula Ia described above can be synthesized using standard techniques. For example, commercially available or readily synthesized perfluoropolyether esters (or functional derivatives thereof) can be combined with a functionalized alkoxysilane, such as a 3-aminopropylalkoxysilane, according to U.S. Pat. No. 3,810,874 (Mitsch et al.).

For certain embodiments, the weight average molecular weight of the polyfluoropolyether segment is about 1000 or higher, more desirably about 1800 or higher. Higher weight average molecular weights further facilitate durability as well as minimizing a potential of bioaccumulation. Generally for ease in use and application, the weight average molecular weight of the polyfluoropolyether segment is desirably about 6000 at most and more desirably about 4000 at most.

Polyfluoropolyether silanes, as indicated above, typically include a distribution of oligomers and/or polymers. Desirably for facilitation of structural integrity of polyfluoropolyether-containing coating as well as minimization of a potential of bioaccumulation the amount of polyfluoropolyether silane (in such a distribution) having a polyfluoropolyether segment having a weight average molecular weight less than 750 is not more than 10% by weight (more desirably not more than 5% by weight, and even more desirably not more than 1% by weight and most desirable 0%) of total amount of polyfluoropolyether silane in said distribution.

For certain embodiments, including any one of the above embodiments, the composition comprising an at least partially fluorinated compound comprising at least one functional group further includes an organic solvent.

For certain embodiments, including any one of the above embodiments wherein the at least partially fluorinated compound comprising at least one functional group is a polyfluoropolyether silane, the polyfluoropolyether silane is desirably applied as a composition comprising the polyfluoropolyether silane and an organic solvent. The organic solvent or blend of organic solvents used typically is capable of dissolving at least about 0.01 percent by weight of the polyfluoropolyether silane, in particular one or more silanes of the Formula Ia. It is desirable that the solvent or mixture of solvents have a solubility for water of at least about 0.1 percent by weight, and for certain of these embodiments, a solubility for acid of at least about 0.01 percent by weight.

Suitable organic solvents, or mixtures of solvents can be selected from aliphatic alcohols, such as methanol, ethanol, and isopropanol; ketones such as acetone and methyl ethyl ketone; esters such as ethyl acetate and methyl formate; ethers such as diethyl ether, diisopropyl ether, methyl t-butyl ether and dipropyleneglycol monomethylether (DPM); hydrocarbon solvents such as alkanes, for example, heptane, decane, and paraffinic solvents; fluorinated hydrocarbons such as perfluorohexane and perfluorooctane; partially fluorinated hydrocarbons, such as pentafluorobutane; hydrofluoroethers such as methyl perfluorobutyl ether and ethyl perfluorobutyl ether. For certain embodiments, including any one of the above embodiments, the organic solvent is a fluorinated solvent, which includes fluorinated hydrocarbons, partially fluorinated hydrocarbons, and hydrofluoroethers. For certain of these embodiments, the fluorinated solvent is a hydrofluoroether. For certain of these embodiments, the hydrofluoroether is methyl perfluorobutyl ether. For certain embodiments, including any one of the above embodiments except where the organic solvent is a fluorinated solvent, the organic solvent is a lower alcohol. For certain of these embodiments, the lower alcohol is selected from the group consisting of methanol, ethanol, isopropanol, and mixtures thereof. For certain of these embodiments, the lower alcohol is ethanol.

For certain embodiments, including any one of the above embodiments where the organic solvent is a lower alcohol and the composition comprises an at least partially fluorinated compound comprising at least one silane group, the composition favorably further comprises an acid. For certain of these embodiments, the acid is selected from the group consisting of acetic acid, citric acid, formic acid, triflic acid, perfluorobutyric acid, sulfuric acid, and hydrochloric acid. For certain of these embodiments, the acid is hydrochloric acid.

The composition comprising an at least partially fluorinated compound comprising at least one functional group may favorably further comprise a non-fluorinated cross-linking agent that is capable of engaging in a cross-linking reaction. Preferably such a cross-linking agent comprises one or more non-fluorinated compounds, each compound having at least two hydrolysable groups. Advantageously such a cross-linking agent comprises one or more non-fluorinated compounds of silicon having at least two hydrolysable groups per molecule. Preferably the hydrolysable groups are directly bonded to the silicon in accordance to Formula II:

$$Si(Y^2)_{4-g}(R^5)_g \qquad \text{II}$$ 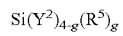

where $R^5$ represents a non-hydrolysable group;
$Y^2$ represents a hydrolysable group; and
g is 0, 1 or 2.

The non-hydrolysable group $R^5$ is generally not capable of hydrolyzing under the conditions used during application of the composition comprising the at least partially compound comprising at least one functional group. For example, the non-hydrolysable group $R^5$ may be independently selected from a hydrocarbon group. If g is 2, the non-hydrolysable groups may the same or different. Preferably g is 0 or 1, more preferably g is 0. The hydrolysable groups $Y^2$ may be the same or different and are generally capable of hydrolyzing under appropriate conditions, for example under acidic or basic aqueous conditions, such that the cross-linking agent can undergo condensation reactions. Preferably, the hydrolysable groups upon hydrolysis yield groups, such as silanol groups capable of undergoing condensation reactions. Typical and preferred examples of hydrolysable groups include those as described with respect to Formula Ia. Preferably, $Y^2$ is an alkoxy, $-OR^6$, more preferably an alkoxy where $R^6$ is a $C_{1-4}$ alkyl.

Representative examples of favorable non-fluorinated silicon compounds for use in a cross-linking agent include tetramethoxysilane, tetraethoxysilane, tetrapropoxysilane, tetrabutoxysilane, methyl triethoxysilane, dimethyldiethoxysilane, octadecyltriethoxy-silane, 3-glycidoxypropyltriethoxysilane, 3-aminopropyltrimethoxysilane, 3-aminopropyl-triethoxysilane, 3-trimethoxysilylpropylmethacrylate and mixtures thereof. Preferably the cross-linking agent comprises $C_1$-$C_4$ tetra-alkoxy derivatives of silicon, more preferably the cross-linking agent comprises tetraethoxysilane.

The amounts by weight of the at least partially fluorinated compound to the non-fluorinated cross-linking agent can change from about 10:1 to about 1:100, preferably from about 1:1 to about 1:50 and most preferably from about 1:2 to about 1:20.

For certain embodiments, e.g. compositions including a hydrolysable group, the composition may further comprise water.

The composition comprising an at least partially fluorinated compound comprising at least one functional group (in particular one silane group), including any one of the above embodiments, can be applied to at least a portion of the surface of the non-metal coating using a variety of coating methods. Such methods include but are not limited to spraying, dipping, spin coating, rolling, brushing, spreading and flow coating. Preferred methods for application include spraying and dipping. For certain embodiments, including any one of the above embodiments, the composition comprising an at least partially fluorinated compound comprising at least one functional group, in any one of its above described embodiments, is applied by dipping at least a portion of the substrate upon which the non-metal coating has been formed in said composition. Alternatively, for certain embodiments, including any one of the above embodiments, the composition comprising the at least partially fluorinated compound comprising at least one functional group, including any one of its above described embodiments, is applied by spraying at least a portion of the substrate upon which the non-metal coating has been formed with said composition.

In preferred embodiments where the composition comprises an at least partially fluorinated compound comprising at least one silane group (in particular a polyfluoropolyether silane or more particularly any one of the embodiments of Formula Ia) and the non-metal coating comprises silicon, oxygen, and hydrogen, for example, with —SiOH groups, upon application of said composition a extremely durable coating is formed through the formation of covalent bonds, including bonds in Si—O—Si groups. For the preparation of such a durable coating, sufficient water should be present to cause hydrolysis of the hydrolyzable groups described above so that condensation to form Si—O—Si groups takes place, and thereby curing takes place. The water can be present either in the treating composition or adsorbed to the substrate surface, for example. Typically, sufficient water is present for the preparation of a durable coating if the application is carried out at room temperature in an atmosphere containing water, for example, an atmosphere having a relative humidity of about 30% to about 80%.

Application is typically carried out by contacting the substrate with the treating composition, generally at room temperature (typically about 20° C. to about 25° C.). Alternatively treating composition can be applied to a substrate that is pre-heated at a temperature of for example between 60° C. and 150° C. Following application the treated substrate can be dried and cured at ambient temperature or (preferably) at elevated temperatures (e.g. at 40° C. to 300° C.), and for a time sufficient to dry and cure. If desired or needed, the treating composition may further comprise a thermal initiator. Alternatively or in addition thereto, following application of the treating composition the treated substrate may be cured (again if desired or needed) by irradiation (e.g. means of UV-irradiators, etc.). Hereto the treating composition typically further comprises a photo-initiator, and curing is performed in a manner known per se, depending on the type and presence, respectively of the photo-initiator used in the treating composition.

A post-treatment process may include a rinsing step (e.g. before or after drying/curing, as desired or needed) to remove excess material, followed by a drying step.

Favorably the thickness of the fluorine-containing coating is at least about 20 nm, preferably at least about 30 nm, and most preferably at least about 50 nm. For certain of these embodiments, the thickness is at most about 300 nm, preferably at most about 200 nm, more preferably at most about 150 nm, and most preferably at most about 100 nm.

For embodiments described herein including a non-metal coating and a fluorine-containing coating, the combined thickness of the two coats may be in the range of about 25 to about 5200 nm. Within this range, favorably the combined thickness of the two coats is less than about 1000 nm, more favorably at most about 950 nm, even more favorably at most about 850 nm, yet even more favorably about 750 nm and most favorably at most about 650 nm.

Additional aspects of the present invention include: devices and components made in accordance with aforesaid methods; a medicinal inhalation device or a component of a medicinal inhalation device comprising a non-metal coating on at least a portion of a surface of the device or the component, as applicable, and a fluorine-containing coating bonded to the non-metal coating wherein the fluorine-containing coating comprises a composition comprising an at least partially fluorinated compound comprising at least functional one group which shares at least one covalent bond with the non-metal coating.

Favorably the fluorine-containing coating is covalently bonded to the non-metal coating through a plurality of covalent bonds, more favorably through covalent bonds including bonds in O—Si groups, more desirably including bonds in Si—O—Si groups. Favorably the non-metal coating (covalently bonded to the fluorine-containing coating) comprises silicon and oxygen, more favorably carbon, silicon and oxygen. Depending on the particular composition of the non-metal coating prior to application of the composition comprising an at least partially fluorinated compound comprising at least one functional group, after application of said composition, the non-metal coating (covalently bonded to the fluorine-containing coating) may or may not comprise hydrogen. Generally however, the non-metal coating (covalently bonded to the fluorine-containing coating) further comprises hydrogen. Desirably the non-metal coating is substantially free of fluorine, more favorably free of fluorine. Desirably the non-metal coating is substantially free of nitrogen, more favorably free of nitrogen. Desirably the non-metal coating is substantially free of sulfur, more favorably free of sulfur. Desirably the non-metal coating is covalently bonded to the at least a portion of a surface of the device or component, as applicable. Desirably the non-metal coating is a plasma deposited coating, and more desirably a plasma deposited coating deposited under ion bombardment conditions. Desirably the non-metal coating is a diamond-like glass coating. Favorably the functional group of the at least partially fluorinated compound is a silane group. Favorably the at least partially fluorinated compound includes a polyfluoropolyether segment, more favorably a perfluorinated polyfluoropolyether segment. Desirably the at least partially fluorinated compound comprising at least one functional group is polyfluoropolyether silane, more desirably a multifunctional polyfluoropolymer silane, and most desirably a difunctional polyfluoropolyether silane. Desirably in such polyfluoropolyether silanes, the polyfluoropolyether segment(s) is (are) linked to the silane segment(s) via a carbon-silicon functionality.

Further aspects of the present invention include: a medicinal inhalation device or a component of a medicinal inhalation device comprising a non-metal coating plasma deposited on at least a portion of a surface of the device or component, respectively, said coating being plasma deposited under ion bombardment conditions and being substantially free (or more favorably) free of fluorine. Desirably the non-metal coating is covalently bonded to the at least a portion of a surface of the device or the component, respectively. Favorably the non-metal coating comprises silicon, oxygen and hydrogen, more favorably carbon, silicon, oxygen and hydrogen. For these embodiments, it is favorable that the silicon to oxygen ratio in the non-metal coating is less than two.

Other aspects of the present invention include: a medicinal inhalation device or a component of a medicinal inhalation device comprising a diamond-like glass coating (as described in detail above) on at least a portion of a surface of the device or component, respectively.

Besides the provision of medicinal inhalation devices and components thereof having desirable surface properties and structural integrity, methods of providing such medicinal inhalation devices and components as described herein are advantageous in their versatility and/or broad applicability to making various components of such medicinal inhalation devices, such components having significantly differing shapes and forms made of significantly differing materials. For example methods described herein can be advantageously used to provide a coating on at least a portion of the interior surface (preferably on the entire interior surface, more preferably the entire surface) of an MDI aerosol container, in particular a conventional MDI aerosol container made of aluminum or an aluminum alloy as well as MDI aerosol containers made of other metals, such as stainless steel. Methods described herein can also be advantageously used to provide a coating on at least a portion of a surface (preferably the entire) surface of a valve stem or a valve body, in particular a valve stem or a valve body made of a polymer such as PBT or acetal. In fact the same method (chemicals, process conditions, etc.) with little or no modification can used to coat aluminum or aluminum alloy MDI containers and metal and/or polymeric valve stems and valve bodies (typically stainless steel and/or PBT and/or acetal) as well as compression springs (typically made of stainless steel) and actuators (typically made of polyethylene or polypropylene). This is particular advantageous for large scale manufacturing and coating as well as stream-lining of manufacturing processing, facilities and/or equipment for coating, while at the same time allowing freedom in regard to the selection of the base material of a component and in some instances expanding the possibilities of the base material for a component.

As detailed above, particular embodiments (in particular those embodiments including a diamond-like glass coating either alone or over-coated with a fluorine-containing coating as described herein) have very favorable impermeability characteristics. These coatings are particular advantageous for use with DPI powder containers or MDI aerosol containers. Moreover due to their very favorable impermeability characteristics, such coatings allow the use of containers, e.g. MDI aerosol containers, made of plastic or other materials which in the past have been ruled out due to the potential of permeation of moisture from outside to the inside, permeation of aerosol formulation through or into the container material and/or extraction of container material into the aerosol formulation. Furthermore, such coatings described herein that are transparent or translucent can be used to provide a transparent or translucent plastic MDI aerosol container which can be advantageous in that a patient can easily monitor the content of the container (i.e. whether it is empty and needs to be replaced).

Methods described herein can also be used to provide other medicinal inhalation devices including nebulizers, pump spray devices, nasal pumps, non-pressurized actuators or components of such devices. Accordingly medicinal inhalation devices or components described herein may also be nebulizers, pump spray devices, nasal pumps, non-pressurized actuators or components of such devices.

Methods described herein can also be used to provide other components used in medicinal inhalation such as breath-actuating devices, breath-coordinating devices, spacers, dose counters, or individual components of such devices, spacers and counters, respectively. Accordingly components described herein may also be breath-actuating devices, breath-coordinating devices, spacers, dose counters, or individual components of such devices, spacers, counters, respectively. In regard to provision of a component or components of dose counters of medicinal inhalation devices, due to desirable surface properties and structural integrity (in particular durability and resistance to wear) of coatings described herein, the provision of such a coating on a component or components (in particular movable component(s) and/or component(s) in contact with a movable component) of a dose counter provides dry lubricity facilitating smooth operation of the dose counter.

Objects and advantages of this invention are further illustrated by the following examples, but the particular materials and amounts thereof recited in these examples, as well as other conditions and details, should not be construed to unduly limit this invention.

EXAMPLES

Preparation of $(CH_3O)_3Si(CH_2)_3N(H)C(O)CF_2O(CF_2CF_2O)_{9-10}(CF_2O)_{9-10}CF_2C(O)N(H)(CH_2)_3Si(OCH_3)_3$ $CH_3OC(O)CF_2O(CF_2CF_2O)_{9-10}(CF_2O)_{9-10}CF_2C(O)OCH_3$ (a perfluoropolyether diester obtained from Solvay Solexis, Houston, Tex., available under the trade designation "FOMBLIN ZDEAL") (50 grams (g)) was added to an oven-dried 100-mL round bottom flask under a nitrogen atmosphere and stirred rapidly at room temperature using a magnetic stirrer. 3-Aminopropyltrimethoxysilane (9.1 g) (obtained from GE Silicones, Wilton, Conn., available under the trade designation "SILQUEST A-1110") was added to the flask in one portion. Initially the mixture was two-phase, and as the reagents mixed the mixture became cloudy. A reaction exotherm to a temperature of about 50° C. was observed, the reaction was continued for 2 hours at 60° C. and then the reaction gradually cooled to room temperature and became a slightly hazy light yellow liquid. The reaction was monitored by gas chromatography (GC) to observe excess 3-aminopropyltrimethoxysilane and Fourier transform infrared spectroscopy (FTIR) to observe unreacted ester functional groups and was found to be complete within 90 minutes after the addition of the 3-aminopropyltrimethoxysilane.

The reaction product was stirred rapidly, and the pressure in the flask was reduced to 1 mmHg (133 Pa) gradually to minimize bumping. Methanol by-product was distilled from the flask over a period of two hours, and 57.5 g of $(CH_3O)_3Si(CH_2)_3N(H)C(O)CF_2O(CF_2CF_2O)_{9-10}(CF_2O)_{9-10}CF_2C(O)N(H)(CH_2)_3Si(OCH_3)_3$ was recovered from the flask. (Average molecular weight is about 2400 and fraction of silane with a polyfluoropolyether segment having a weight average MW lower than 750 is zero).

Unless specified otherwise, plasma treatment followed by silane treatment as described in the following were performed in the Examples.

Plasma Treatment Method

Exemplary components/substrates were treated in batch plasma system Plasmatherm Model 3032, available from Plasmatherm, Kresson, N.J., which was configured for reactive ion etching with a 26-inch lower RF-powered electrode insulated from the chamber by a PTFE support and central gas pumping. The grounded chamber was connected to a roots style blower (Edwards Model EH1200, Boc Edwards, West Sussex, United Kingdom) backed by a dry mechanical pump (Edwards Model iQDP80, Boc Edwards). Plasma was powered by a 5 kW, 13.56 MHz solid-state generator (RF Plasma Products Model RF50S0, available from MKS Power Generators and Subsystems, Wilmington, Mass.) and a radio frequency impedance matching network (Plasmatherm Model AMN-30, available from Plasmatherm). The system had a nominal base pressure of 5 mTorr (0.67 Pa). The flow rates of gases were controlled by flow controllers available from MKS Power Generators and Subsystems. Components/substrates for deposition were placed on the lower powered electrode (and thus were located with the ion sheath formed upon plasma generation).

The plasma treatment included the following steps:

Step 1. Exemplary components/substrates were first treated in an oxygen plasma by flowing oxygen gas (99.99%, UHP Grade, available from Scott Specialty Gases, Plumsteadville, Pa.), at 500 standard cubic centimeters per minute (sccm) flow rate and maintaining the pressure at 52 millitorr (mtorr) (6.9 Pascals (Pa)) and plasma power of 1000 watts. The oxygen priming step was carried out for 60 seconds.

Step 2. Following the oxygen plasma priming, tetramethylsilane (99.9%, NMR Grade, available from Sigma-Aldrich Chemicals, St. Louis, Mo.) was introduced. Tetramethylsilane vapor was introduced into the chamber at a flow rate of 150 sccm while the oxygen flow was maintained at 500 sccm. The pressure was held at 64 mtorr (8.5 Pa), and plasma power was held at 1000 watts. The treatment time was 60 seconds, deposition rate about 170 nm/min.

Step 3. The tetramethylsilane gas was then shut off and the oxygen gas continued to run at a flow of 500 sccm. The pressure was maintained at 52 mtorr (6.9 Pa), and plasma power delivered at 1000 watts. This final step of post-deposition oxygen plasma treatment lasted 60 seconds.

The power density used in each step was 0.27 watts/square cm.

Typically batches of up to 50 exemplary components/substrates were placed in a tray on the lower powered electrode and the aforesaid three-step-treatment was conducted three times. Between treatments, the chamber was vented to atmosphere and the tray was removed, shaken (to redistribute the components/substrates and their position on the tray), and then re-placed onto the lower powered electrode.

Specimen Micro-hardness (H) and Elastic Modulus (E) of such deposited coatings on silicon wafer substrates were determined using a MTS DCM Nanoindenter supplied by MTS Nano Instruments, 701 Scarboro Road Suite 100 Oak Ridge, Tenn. 37830. The coatings were tested probing the sample from the top surface. For all experiments a diamond Berkovich probe was used. Spatial drift was held at a maximum of 0.01 nm/s maximum. A constant strain rate experiment was run at 0.05/s to command depths of 100 nm and in some cases 200 nm, to establish a depth for which the results would be effectively independent of the substrate—this depth was 50 nm. The dynamic excitation frequency, 75 hz, and amplitude of the indenter, 1 nm, were held constant. Results are quoted for 10-15 measurements taken at different positions on the sample.

Micro-hardness and Elastic Modulus of deposited coatings using the same test method as described above were determined except that the coating was not deposited under conditions of ion bombardment. In one case the substrate was placed at a floating potential and positioned so that the substrate was outside the ion sheath, and in another case the system was modified to include a grounded electrode (instead of the chamber acting as the grounded electrode) and the substrate was placed on a grounded electrode.

Microhardness determined for plasma-deposited coatings deposited under conditions of ion bombardment (i.e. substrate was positioned on powered electrode) was 2.5 GPa, compared with 0.7 GPa (floating potential) and 0.2 GPa (grounded electrode).

Elastic Modulus determined for plasma-deposited coatings deposited under conditions of ion bombardment (i.e. where substrate was positioned on powered electrode) was 17.5 GPa, compared with 9.2 GPa (floating potential) and 2.6 GPa (grounded electrode).

Silane Treatment Method

A solution (3 liters (L)) of 0.1% $(CH_3O)_3Si(CH_2)_3N(H)C(O)CF_2(CF_2CF_2O)_{9-10}(CF_2O)_{9-10}CF_2C(O)N(H)(CH_2)_3Si(OCH_3)_3$ in HFE-7100 fluid (available from 3M Company, St. Paul, Minn. under the trade designation "NOVEC HFE-7100") was placed in a 4-L beaker at room temperature. The beaker was placed in a dip coater. Each exemplary component/substrate, which had been plasma-treated according to the method described above, was fixed vertically above the solution, introduced and submerged entirely into the solution and held in place for at least five seconds. Exemplary component(s) was (were) withdrawn from the solution allowed to drain and then placed in an aluminum pan. The pan was then placed in an oven at 120° C. for 60 minutes. Exemplary components were then allowed to stand at least 24 hours. Thickness of coatings provided through this silane treatment method typically ranged from about 20 to 100 nm.

Example 1

Stainless steel compression springs and stainless steel primary valve bodies for metered dose valves of the type marketed under the trade designation SPRAYMISER (3M Company, St. Paul, Minn., USA) having a 50 mcl metering chamber were treated. Coated components were then built into valves. Also control valves were constructed using uncoated springs and primary valve bodies.

As a model substance for particulate drug, Brilliant blue food dye (commercially available from Warner Jenkinson Europe Ltd. Oldmeadow Road, King's Lynn, Norfolk, PE 30 4 LA, UK), micronized using a fluid energy mill to give a majority of particles in the range of 1 to 3 microns, was used.

In order to evaluate the properties of the exemplary valves including coated components in comparison to the control valves, valves (3 exemplary valves and 3 control valves) were crimped onto cans containing the following model formulation to provide six test units.

| Formulation #1 | mg/ml | % w/w |
| --- | --- | --- |
| Micronized Brilliant Blue food dye | 0.132 | 0.0109 |
| Sub-micron anhydrous Lactose* | 2.64 | 0.2179 |
| Oleic acid | 0.0606 | 0.0050 |
| Dehydrated ethanol | 24.2285 | 2.0000 |
| HFA 134a | 1184.3653 | 97.7662 |

*micronized lactose monohydrate obtained from DMV International Pharma under the trade designation Pharmatose 325M was processed using an Avestin C50 high pressure homogenizer to give a majority of particles in the range of 0.2 to 1 micron.

Each test unit was primed using 5 actuations and then actuated 50 times. Subsequently the units were chilled down to −60° C. and the valves detached from the cans. The valves were carefully disassembled. Each spring and primary valve body was washed with 10 ml deionized water to quantitatively collect any Brilliant Blue food dye deposit on said component, and the amount of dye collected was determined via photospectrometric determination of light absorbance at 629 nm wavelength. The results are summarized in the following table (Table 1).

TABLE 1

|  | Compression spring: mcg of brilliant blue | Primary valve body: mcg of brilliant blue |
|---|---|---|
| Example 1 | | |
| Unit A | 1.5 | 3.4 |
| Unit B | 1.4 | 3.9 |
| Unit C | 2.5 | 3.7 |
| Control | | |
| Unit A | 11.0 | 11.9 |
| Unit B | 7.6 | 7.8 |
| Unit C | 9.2 | 14.1 |

Example 2

Acetal valve stems and PBT primary valve bodies for valves of the type marketed under the trade designation BK357 (Bespak plc, Bergen Way, Kings Lynn Norfolk PE 30 2JJ) having a 50 mcl metering chamber were treated. Coated components were then built into valves. Valves with non-coated valve stems and primary valve bodies served as controls. Valves (3 exemplary valves and 3 control valves) were crimped onto cans containing the following model formulation to provide six test units.

| Formulation #2 | mg/ml | % w/w |
|---|---|---|
| Micronized Brilliant Blue food dye, as described above | 1.2 | 0.0091 |
| Oleic acid | 0.0606 | 0.0050 |
| Dehydrated ethanol | 24.2285 | 2.0000 |
| HFA 134a | 1185.9373 | 97.8959 |

Each test unit was primed using 5 actuations and then actuated 89 times. Subsequently, using a JJ Lloyd tensile tester, the valve force profile (force required to actuate and force applied by the valve stem on the valve return stroke) of each of the unit was measured (3 repeats; 3 actuations), and then the friction between the valve stem and seals (i.e. the valve friction) computed. The determined mean values for valve frictions are given in Table 2. The determined return forces for the metering valves with treated components were in the range of 6.4 to 9.7 Newtons. After force measurements, the units were chilled down to −60° C. and the valves detached from the cans. The valves were carefully disassembled, and deposition on each valve stem and primary valve body was determined as described in Example 1, the results are summarized in Table 2.

TABLE 2

|  | Valve friction Newtons | Valve Stem: mcg of brilliant blue | Primary Valve body: mcg of brilliant blue |
|---|---|---|---|
| Example 2 | | | |
| Unit A | 7.5 | 11 | 34 |
| Unit B | 7.2 | 8 | 16 |
| Unit C | 9.0 | 14 | 21 |

TABLE 2-continued

|  | Valve friction Newtons | Valve Stem: mcg of brilliant blue | Primary Valve body: mcg of brilliant blue |
|---|---|---|---|
| Control | | | |
| Unit A | 9.9 | 49 | 83 |
| Unit B | 10.6 | 31 | 125 |
| Unit C | 10.2 | 38 | 73 |

Example 3

Compression springs, primary valve bodies and machined valve stems, all made of stainless steel for metered dose valves of the type similar to that shown in FIG. 1 having a 63 mcl metering chamber were treated. Treated components were then built into valves. Also control valves were constructed in the conventional manner using untreated compression springs, primary valve bodies and machined valve stems. Valves (5 exemplary valves and 5 control valves) were crimped onto cans containing a formulation consisting of 1.97 mg/ml albuterol sulfate (having a majority of particles in the range of 1 to 3 microns) and HFA 134a to provide ten test units. Each test unit was primed using 5 actuations and then actuated 200 times. Subsequently, the valve force profile (force required to actuate and force applied by the valve stem on the valve return stroke) of each of the unit was measured as described Example 2. Determined valve friction results are reported in Table 3, and return force for metered dose valves assembled with treated components was found to be in the range 5.8 to 11.6 Newtons. Similar to Example 2 deposition measurements were carried out. Here, units were punctured to eject the remaining liquid contents, and the valves detached and carefully disassembled. Each component to be assayed for drug was placed in a lidded tube. 5 ml of sample diluent (45:55 Methanol:0.1% Phosphoric Acid Solution) was dispensed into each tube, replacing lids immediately after dispensing the diluent. Each tube was then placed in a sonic bath for 2 minutes then shaken gently by inversion and swirling for 1 minute to collect quantitatively any albuterol sulfate deposit on said component. An aliquot from each tube was then transferred for analysis by HPLC to determine the amount of albuterol sulfate deposited. The results are summarized in Table 3.

TABLE 3

|  | Valve friction Newtons | Compression Spring: | Valve Stem: | Primary Valve body: |
|---|---|---|---|---|
|  |  | mcg of albuterol sulfate | | |
| Example 3 | | | | |
| Unit A | 11.7 | 152.7 | * | 156.5 |
| Unit B | 6.1 | 301.7 | 73.7 | 222.1 |
| Unit C | 13.2 | 243.4 | 90.5 | 171.5 |
| Unit D | 12.2 | 144.3 | 69.6 | 115.5 |
| Unit E | 9.8 | 243.7 | 85.0 | 255.9 |
| Control | | | | |
| Unit A | 18.8 | 1252.1 | 616.4 | 515.0 |
| Unit B | 18.0 | 1636.0 | 611.3 | 492.1 |
| Unit C | 16.9 | 1064.5 | 419.0 | 404.9 |
| Unit D | 18.5 | 1140.3 | 604.7 | 388.0 |
| Unit E | 17.1 | 1233.3 | 547.0 | 342.8 |

* not measured due to contamination of sample

Example 4

In this example, exemplary components/substrates were treated with the following Tumbling Plasma Treatment Method to provide components with just a diamond-like-glass coating.

Tumbling Plasma Treatment Method

Exemplary components/substrates were treated in a custom-built, tumbling cylindrical plasma system. The chamber is a quartz tube (with four internal baffles) which is 15 cm in diameter and 30 cm long, to which aluminum end flanges are attached by means of a vacuum grade sealant (Ton-Seal). Each of the end-flanges is provided with a 1.5 inch diameter stainless tube, where one is connected via a rotary seal to roots style blower (Alcatel Model RSV600, Annecy, France) backed by a mechanical pump (Leybold Model D65BCS, Export, Pa., USA), and the other connected via a rotary seal to a gas supply system. Plasma was generated by a 6 mm thick copper external electrode, 15 cm wide and 25 cm long, located below the quartz tube whose axis is horizontal. The copper electrode was rolled into an arc of a circle so that the 15 cm width of the electrode was conformed to the curvature of the quartz tube but separated from the tube by a gap of 2 mm. The entire quartz tube assembly was housed inside a housing constructed from perforated sheet metal which served to act as the grounded counter electrode and also the Faraday shield, preventing the electromagnetic radiation from escaping into free space surrounding the plasma system. The smaller powered electrode located within a much larger perforated metal ground structure constituted an asymmetric plasma system. Plasma was powered by a 1 kW, 13.56 MHz solid-state generator (Seren, Model No. R1001, available from Seren IPS, Inc., Vineland, N.J., USA) and a radio frequency impedance matching network (Rf Plasma Products Model AMN-10, available from Advanced Energy, Fort Collins, Colo.). The system had a nominal base pressure of 5 mTorr (0.67 Pa). The flow rates of gases were controlled by flow controllers available from MKS Power Generators and Subsystems, Wilmington, Mass. Components/substrates for deposition were placed inside the quartz tube and were essentially located within the ion sheath adjacent to the powered electrode, said powered electrode being located just underneath the quartz tube. The quartz tube was rotated constantly at a slow speed of 1.2 revolutions per minute.

The plasma treatment included the following steps, each step using a power density of 0.53 watts/square cm:

Step 1. Exemplary components/substrates were first treated in an oxygen plasma by flowing oxygen gas (99.99%, UHP Grade, available from Scott Specialty Gases, Plumsteadville, Pa.), at 100 standard cubic centimeters per minute (sccm) flow rate and maintaining the pressure at 120 millitorr (mtorr) (15.9 Pascals (Pa)) and plasma power of 200 watts. The oxygen priming step was carried out for 300 seconds.

Step 2. Following the oxygen plasma priming, tetramethylsilane (99.9%, NMR Grade, available from Sigma-Aldrich Chemicals, St. Louis, Mo.) was introduced. Tetramethylsilane vapor was introduced into the chamber at a flow rate of 60 sccm while the oxygen flow was maintained at 30 sccm. The pressure was held at 100-150 mtorr (13-20 Pa), and plasma power was held at 200 watts. The treatment time was 900 seconds.

(A post-treatment with oxygen plasma was not performed in order to leave the deposited diamond-like-glass film in its native, deposited surface condition.)

Typically batches of up to 500 exemplary components/substrates were placed inside the quartz tube and the tube rotated at 1.2 revolutions per minute while the plasma treatment steps 1 and 2 were being done. Between deposition runs, deposition build-up on the quartz wall was cleaned off by using an abrasive pad followed by vacuuming of the resulting dust; said cleaning was done in order to prevent any potential of material/build-up from previous run(s) on the quartz wall flaking off during deposition, getting incorporated into the growing thin film and causing defects in said growing film. After the deposition of the film the quartz tube chamber was vented to atmosphere and the components taken out.

Compression springs, primary valve bodies and machined valve stems of the type used in Example 3 were treated using the aforesaid Tumbling Plasma Treatment Method. Treated components were then built into valves, and the valves (5 exemplary valves) were crimped onto cans containing an albuterol sulfate formulation of the type used in Example 3, where albuterol-sulfate-deposition measurements were carried out as described in Example 3. The results are summarized in Table 4.

TABLE 4

| Example 4 | Compression Spring: | Valve Stem: | Primary Valve body: |
|---|---|---|---|
| | mcg of albuterol sulfate | | |
| Unit A | 190.7 | 107.1 | 113.4 |
| Unit B | 134.6 | 92.9 | 165.1 |
| Unit C | 180.1 | 109.6 | 178.2 |
| Unit D | 171.8 | 94.8 | 162.8 |
| Unit E | 125.2 | 106.5 | 64.2 |

The invention claimed is:

1. A method of making a medicinal inhalation device or a component of a medicinal inhalation device comprising:
    a) forming a non-metal coating on at least a portion of a surface of the device or the component, respectively, said coating having at least one functional group;
    b) applying to at least a portion of a surface of the non-metal coating a composition comprising an at least partially fluorinated compound comprising at least one functional group; and
    c) allowing at least one functional group of the at least partially fluorinated compound to react with at least one functional group of the non-metal coating to form a covalent bond.

2. A method according to claim 1, wherein said at least one functional group of the non-metal coating has an active hydrogen.

3. A method according to claim 1, wherein the non-metal coating is formed by plasma deposition.

4. A method according to claim 3, wherein the non-metal coating is formed by plasma deposition under ion bombardment conditions.

5. A method according claim 1, wherein the non-metal coating comprises silicon, oxygen and hydrogen.

6. A method according to claim 5, wherein the non-metal coating further comprises carbon.

7. A method according to claim 6, wherein the non-metal coating comprises a micro-hardness of at least 1 GPa comprising on a hydrogen free basis at least about 20 atomic percent carbon and at least about 30 atomic percent of silicon+oxygen.

8. A method according to claim 5, wherein the silicon to oxygen ratio in the non-metal coating is less than two.

9. A method according to claim 1, wherein said at least partially fluorinated compound is selected from: (i) a compound that comprises a hydrolysable group; (ii) a compound that comprises a silane group; (iii) a compound that comprises a polyfluoropolyether segment; and (iv) a compound that comprises a polyfluoropolyether silane.

10. A method according to claim 9, wherein said at least partially fluorinated compound comprises a polyfluoropolyether segment, wherein the polyfluoropolyether segment has weight average molecular weight of about 1000 or higher and/or is a perfluorinated polyfluoropolyether segment, wherein the repeating units of the perfluorinated polyfluoropolyether segment the number of carbon atoms in sequence is at most 6.

11. A medicinal inhalation device or a component of a medicinal inhalation device comprising a non-metal coating on at least a portion of a surface of the device or the component, respectively, and a fluorine-containing coating bonded to the non-metal coating wherein the fluorine-containing coating comprises an at least partially fluorinated compound comprising at least one functional group which shares at least one covalent bond with the non-metal coating.

12. A device or a component according to claim 11, wherein the fluorine-containing coating is covalently bonded to the non-metal coating through a plurality of covalent bonds, in particular a plurality of covalent bonds including bonds in O—Si groups, more particularly bonds in Si—O—Si groups.

13. A medicinal inhalation device or a component of a medicinal inhalation device comprising a non-metal coating plasma deposited on at least a portion of a surface of the device or the component, respectively, said coating being plasma deposited under ion bombardment conditions and comprising about 1 atomic percent of fluorine or less.

14. A medicinal inhalation device or a component of a medicinal inhalation device comprising a coating comprising a micro-hardness of at least 1 GPa on at least a portion of a surface of the device or the component, respectively.

* * * * *

UNITED STATES PATENT AND TRADEMARK OFFICE
CERTIFICATE OF CORRECTION

PATENT NO.        : 8,430,097 B2
APPLICATION NO.   : 12/741530
DATED             : April 30, 2013
INVENTOR(S)       : Philip Jinks et al.

It is certified that error appears in the above-identified patent and that said Letters Patent is hereby corrected as shown below:

On the Title Page, Column 1
Under "Inventors", line 2, delete "MA" and insert -- MN --, therefor.
Under "Assignee", line 2, delete "MO" and insert -- MN --, therefor.

In the Specification

Column 4
Line 12, after "thereof" insert -- . --.

Column 7
Line 14, after "groups" insert -- . --.

Column 14
Line 28, delete "deaglomeration" and insert -- deagglomeration --, therefor.
Line 50, after "227" insert -- . --.

Column 15
Line 16, after "list" insert -- . --.

Column 19
Line 50, delete "deaglomeration" and insert -- deagglomeration --, therefor Column 21
Line 21, delete "nanoidenter" and insert -- nanoindenter --, therefor.
Line 32, delete "nanoidenter" and insert -- nanoindenter --, therefor.

Column 24
Line 17, delete "Ton)." and insert -- Torr). --, therefor.

Signed and Sealed this
Second Day of December, 2014

Michelle K. Lee
*Deputy Director of the United States Patent and Trademark Office*

Column 27
Lines 28-29, delete "polyfluoropolyethersilane." and insert -- polyfluoropolyether silane. --, therefor.
Line 62, after "strength" insert -- . --.

Column 41
Line 37, delete "Rf" and insert -- RF --, therefor.

In the Claims

Column 42
Line 57, in claim 5, after "according" insert -- to --.